US007306901B2

(12) United States Patent
Kemp et al.

(10) Patent No.: US 7,306,901 B2
(45) Date of Patent: Dec. 11, 2007

(54) METHODS AND MEANS FOR ASSESSING HIV ENVELOPE INHIBITOR THERAPY

(75) Inventors: Sharon Kemp, Cambridgeshire (GB); Johan Hendrika Jozef Vingerhoets, Wijnegem (BE); Lieve Emma Jan Michiels, Mol (BE)

(73) Assignee: Tibotec Pharmaceuticals, Ltd. (IE)

( * ) Notice: Subject to any disclaimer, the term of this patent is extended or adjusted under 35 U.S.C. 154(b) by 0 days.

(21) Appl. No.: 10/214,670

(22) Filed: Aug. 8, 2002

(65) Prior Publication Data

US 2003/0180715 A1 Sep. 25, 2003

(30) Foreign Application Priority Data

Aug. 8, 2001 (EP) .................................. 01203011

(51) Int. Cl.
*C12Q 1/68* (2006.01)
*C12Q 1/70* (2006.01)
*A61K 39/21* (2006.01)

(52) U.S. Cl. ............................ 435/5; 435/6; 424/208.1

(58) Field of Classification Search .................... 435/5, 435/6; 536/23.72; 424/208.1
See application file for complete search history.

(56) References Cited

U.S. PATENT DOCUMENTS 6,033,902 A 3/2000 Haseltine et al.

FOREIGN PATENT DOCUMENTS

| | | |
|---|---|---|
| EP | 1 043 407 A2 | 10/2000 |
| WO | WO 94/17825 | 8/1994 |
| WO | WO 97/27480 | 7/1997 |
| WO | WO 00/66774 | 11/2000 |
| WO | WO 00/73511 A1 | 12/2000 |
| WO | WO 01/57245 A2 | 8/2001 |

OTHER PUBLICATIONS

Zöllner et al. AIDS, May 4, 2001, vol. 15, Issue 7, pp. 935-936, internet printout pages numbered as pp. 1-3.*

Holodniy, M. Business Briefings: Long-Term Healthcare, 2004, pp. 50-52 Available from website: http://www.bbriefings.com/cdps/cditem.cfm?NID=886.*

Kellam et al. Recombinant Virus Assay, Antimicrobial Agents and Chemotherapy, 1994, vol. 38, No. 1, pp. 23-30.*

Kilby et al. Potent suppression of HIV-1 replication in humans by T-20, Nature Medicine, 1998, vol. 4, No. 11, pp. 1302-1307.*

PCT/IB97/00071, Int'l Search Report (2 sheets), Jul. 31, 1997, mailed Jun. 24, 1997.

PCT/EP00/04915, Int'l Search Report (4 sheets), Dec. 7, 2000, mailed Nov. 7, 2000.

PCT/US93/12088, Int'l Search Report (2 sheets), Aug. 18, 1994, mailed Mar. 29, 1994.

* cited by examiner

*Primary Examiner*—Stacy B. Chen
(74) *Attorney, Agent, or Firm*—Woodcock Washburn LLP

(57) ABSTRACT

The present invention relates to methods and products for the evaluation of HIV treatment. In particular, molecular events at the HIV envelope protein and their effect on therapeutic efficacy of drugs are determined. The methods rely on providing HIV envelope nucleic acid material and evaluating a treatment either through genotyping or phenotyping. Said method may find use in multiple fields including diagnostics, drug screening, pharmacogenetics and drug development.

5 Claims, 10 Drawing Sheets

Figure 8

| | | | | | | | | | | | | | | | | | | | | |
|---|---|---|---|---|---|---|---|---|---|---|---|---|---|---|---|---|---|---|---|---|
| HXB2D | K | I | E | P | L | G | V | A | P | T | K | A | K | R | R | V | V | Q | R | E |
| 133275 | R | I | E | P | L | G | V | A | P | T | E | A | K | R | R | V | V | Q | R | E |
| 133276 | Q | I | E | P | L | G | V | A | P | T | K | A | K | R | R | V | V | Q | R | E |
| 133268 | R | I | E | P | L | G | I | A | P | N | K | A | K | R | R | V | V | Q | R | E |
| 142028 | K | I | E | P | L | G | V | A | P | T | K | A | K | R | R | V | V | Q | R | E |

↓ start gp41 coding sequence

| | | | | | | | | | | | | | | | | | | | | |
|---|---|---|---|---|---|---|---|---|---|---|---|---|---|---|---|---|---|---|---|---|
| HXB2D | K | R | A | V | G | - | I | G | A | L | F | L | G | F | L | G | A | A | G | S |
| 133275 | K | R | A | V | V | G | I | G | A | L | F | L | G | F | L | G | T | A | G | S |
| 133276 | K | R | A | V | G | A | I | G | A | M | F | L | G | F | L | G | A | A | G | S |
| 133268 | K | R | A | I | G | A | L | G | A | M | F | L | G | F | L | G | T | A | G | S |
| 124028 | K | R | A | V | G | - | I | G | A | M | F | L | G | F | L | G | A | A | G | S |

| | | | | | | | | | | | | | | | | | | | | |
|---|---|---|---|---|---|---|---|---|---|---|---|---|---|---|---|---|---|---|---|---|
| HXB2D | T | M | G | A | A | S | M | T | L | T | V | Q | A | R | Q | L | L | S | G | I |
| 133275 | T | M | G | A | A | S | L | T | L | T | V | Q | A | R | Q | L | L | S | G | I |
| 133276 | T | M | G | A | A | S | M | A | L | T | V | Q | A | R | Q | L | L | S | G | I |
| 133268 | T | M | G | A | A | S | L | T | L | T | V | Q | A | R | Q | L | L | S | G | I |
| 142028 | T | M | G | A | A | S | L | T | L | T | V | Q | A | R | Q | L | L | S | G | I |

| | | | | | | | | | | | | | | | | | | | | |
|---|---|---|---|---|---|---|---|---|---|---|---|---|---|---|---|---|---|---|---|---|
| HXB2D | V | Q | Q | Q | N | N | L | L | R | A | I | E | A | Q | Q | H | L | L | Q | L |
| 133275 | V | Q | Q | Q | N | N | L | L | R | A | I | E | A | Q | Q | H | L | L | Q | L |
| 133276 | V | Q | Q | Q | N | N | L | L | R | A | I | E | A | Q | Q | H | L | L | Q | L |
| 133268 | V | Q | Q | Q | N | N | L | L | R | A | I | E | A | Q | Q | H | L | L | Q | L |
| 142028 | V | Q | Q | Q | N | N | L | L | R | A | I | E | A | Q | Q | H | L | L | Q | L |

| | | | | | | | | | | | | | | | | | | | | |
|---|---|---|---|---|---|---|---|---|---|---|---|---|---|---|---|---|---|---|---|---|
| HXB2D | T | V | W | G | I | K | Q | L | Q | A | R | I | L | A | V | E | R | Y | L | K |
| 133275 | T | V | W | G | I | K | Q | L | Q | A | R | V | L | A | V | E | R | Y | L | R |
| 133276 | T | V | W | G | I | K | Q | L | Q | A | R | V | L | A | V | E | R | Y | L | K |
| 133268 | T | V | W | G | I | K | Q | L | Q | A | R | V | L | A | V | E | R | Y | L | Q |
| 142028 | T | V | W | G | I | K | Q | L | Q | A | R | V | L | A | V | E | R | Y | L | K |

| | | | | | | | | | | | | | | | | | | | | |
|---|---|---|---|---|---|---|---|---|---|---|---|---|---|---|---|---|---|---|---|---|
| HXB2D | D | Q | Q | L | L | G | I | W | G | C | S | G | K | L | I | C | T | T | A | V |
| 133275 | D | Q | Q | L | L | G | I | W | G | C | S | G | K | L | I | C | T | T | T | V |
| 133276 | D | Q | Q | L | L | G | I | W | G | C | S | G | K | L | I | C | T | T | A | V |
| 133268 | D | Q | Q | L | L | G | I | W | G | C | S | G | K | L | I | C | T | T | S | V |
| 142028 | D | Q | Q | L | L | G | I | W | G | C | S | G | K | L | I | C | T | T | A | V |

Figure 8 continued:

| | | | | | | | | | | | | | | | | | | | | |
|---|---|---|---|---|---|---|---|---|---|---|---|---|---|---|---|---|---|---|---|---|
| HXB2D | P | W | N | A | S | W | S | N | K | S | L | E | Q | I | W | N | H | T | T | W |
| 133275 | P | W | N | T | S | W | S | N | K | T | L | N | E | I | W | D | N | M | T | W |
| 133276 | P | W | N | T | S | W | S | N | K | S | L | S | Q | I | W | D | N | M | T | W |
| 133268 | P | W | N | D | S | W | S | N | K | T | Y | G | E | I | W | G | N | M | T | W |
| 142028 | P | W | N | D | S | W | S | N | K | T | M | D | Q | I | W | N | N | M | T | W |

| | | | | | | | | | | | | | | | | | | | | |
|---|---|---|---|---|---|---|---|---|---|---|---|---|---|---|---|---|---|---|---|---|
| HXB2D | M | E | W | D | R | E | I | N | N | Y | T | S | L | I | H | S | L | I | E | E |
| 133275 | M | E | W | D | R | Q | I | S | N | Y | T | E | V | I | Y | S | L | L | E | E |
| 133276 | M | E | W | E | R | E | I | D | N | Y | T | G | L | I | Y | N | L | I | E | E |
| 133268 | M | Q | W | D | R | E | I | N | N | Y | T | G | L | I | Y | T | L | L | E | E |
| 142028 | M | D | W | E | K | E | I | D | N | Y | T | S | L | I | Y | N | L | I | E | E |

| | | | | | | | | | | | | | | | | | | | | |
|---|---|---|---|---|---|---|---|---|---|---|---|---|---|---|---|---|---|---|---|---|
| HXB2D | S | Q | N | Q | Q | E | K | N | E | Q | E | L | L | E | L | D | K | W | A | S |
| 133275 | S | Q | N | Q | Q | E | K | N | E | Q | E | L | L | A | L | D | K | W | A | S |
| 133276 | S | Q | N | Q | Q | E | K | N | E | K | D | L | L | E | L | N | S | W | A | S |
| 133268 | S | Q | H | Q | Q | E | K | N | E | Q | D | L | L | A | L | D | Q | W | A | S |
| 142028 | S | Q | N | Q | Q | D | K | N | E | Q | E | L | L | E | L | D | K | W | A | S |

| | | | | | | | | | | | | | | | | | | | | |
|---|---|---|---|---|---|---|---|---|---|---|---|---|---|---|---|---|---|---|---|---|
| HXB2D | L | W | N | W | F | N | I | T | N | W | L | W | Y | I | K | L | F | I | M | I |
| 133275 | L | W | N | W | F | D | I | T | K | W | L | W | Y | I | K | I | F | I | M | I |
| 133276 | L | W | N | W | F | D | I | S | N | W | L | W | Y | I | K | I | F | I | M | I |
| 133268 | L | W | N | W | F | D | I | S | N | W | L | W | Y | I | K | I | F | I | M | I |
| 142028 | L | W | N | W | F | N | I | T | N | W | L | W | Y | I | K | I | F | I | M | I |

| | | | | | | | | | | | | | | | | | | | | |
|---|---|---|---|---|---|---|---|---|---|---|---|---|---|---|---|---|---|---|---|---|
| HXB2D | V | G | G | L | V | G | L | R | I | V | F | A | V | L | S | I | V | N | R | V |
| 133275 | V | G | G | L | V | G | L | R | I | V | F | T | V | L | S | I | V | N | R | V |
| 133276 | V | G | G | L | I | G | L | R | I | V | F | A | V | L | S | I | V | N | R | V |
| 133268 | V | G | G | L | I | G | L | R | I | V | F | A | V | L | S | I | V | N | R | V |
| 142028 | I | G | G | L | V | G | L | R | I | V | F | A | V | V | S | I | V | N | R | V |

| | | | | | | | | | | | | | | | | | | | | |
|---|---|---|---|---|---|---|---|---|---|---|---|---|---|---|---|---|---|---|---|---|
| HXB2D | R | Q | G | Y | S | P | L | S | F | Q | T | H | L | P | I | P | R | G | P | D |
| 133275 | R | Q | G | Y | S | P | L | S | F | Q | T | H | L | P | T | P | R | G | P | D |
| 133276 | R | Q | G | Y | S | P | L | S | F | Q | T | L | L | P | A | S | R | G | P | D |
| 133268 | R | Q | G | Y | S | P | L | S | F | Q | T | H | F | P | A | P | R | G | P | D |
| 142028 | R | Q | G | Y | S | P | L | S | F | Q | T | R | L | P | A | P | R | G | P | D |

| | | | | | | | | | | | | | | | | | | | | |
|---|---|---|---|---|---|---|---|---|---|---|---|---|---|---|---|---|---|---|---|---|
| HXB2D | R | P | E | G | I | E | E | E | G | G | E | R | D | R | D | R | S | I | R | L |
| 133275 | R | P | E | G | I | E | G | E | G | G | D | K | D | R | D | R | S | S | G | L |
| 133276 | R | P | E | G | I | E | E | E | G | G | E | R | D | R | D | R | S | V | R | L |
| 133268 | R | P | E | G | T | E | E | E | G | G | E | R | D | R | D | R | S | T | R | L |
| 142028 | R | P | E | G | I | E | E | E | G | G | E | Q | D | R | D | R | S | G | R | L |

Figure 8 continued

| | | | | | | | | | | | | | | | | | | | | |
|---|---|---|---|---|---|---|---|---|---|---|---|---|---|---|---|---|---|---|---|---|
| HXB2D | V | N | G | S | L | A | L | I | W | D | D | L | R | S | L | C | L | F | S | Y |
| 133275 | V | T | G | F | L | A | L | I | W | V | D | L | R | N | L | F | L | F | S | Y |
| 133276 | V | N | G | F | L | A | L | V | W | D | D | L | R | S | L | C | L | F | S | Y |
| 133268 | V | H | G | L | L | P | L | V | W | D | D | L | R | S | L | C | L | F | S | Y |
| 142028 | V | D | G | L | L | A | L | I | W | V | D | L | R | S | L | C | L | F | S | Y |

| | | | | | | | | | | | | | | | | | | | | |
|---|---|---|---|---|---|---|---|---|---|---|---|---|---|---|---|---|---|---|---|---|
| HXB2D | H | R | L | R | D | L | L | L | I | V | T | R | I | V | E | L | L | G | R | R |
| 133275 | H | R | L | R | D | L | L | L | I | V | T | R | I | V | E | L | L | G | R | G |
| 133276 | H | R | L | R | D | L | L | L | I | V | A | R | T | V | E | L | L | G | R | R |
| 133268 | H | R | L | R | D | L | L | L | I | A | A | R | I | V | E | L | L | G | R | R |
| 142028 | H | R | L | R | D | L | L | L | I | L | T | R | I | V | E | L | L | G | R | R |

| | | | | | | | | | | | | | | | | | | | | |
|---|---|---|---|---|---|---|---|---|---|---|---|---|---|---|---|---|---|---|---|---|
| HXB2D | G | W | E | A | L | K | Y | W | W | N | L | L | Q | Y | W | S | Q | E | L | K |
| 133275 | G | W | E | T | L | K | Y | W | W | N | L | L | Q | Y | W | S | Q | E | L | K |
| 133276 | G | W | E | I | L | K | Y | W | G | N | L | L | Q | Y | W | S | Q | E | I | R |
| 133268 | G | W | E | A | L | K | Y | R | W | N | L | L | Q | Y | W | L | Q | E | L | K |
| 142028 | G | W | E | A | L | K | Y | W | W | N | L | L | Q | Y | W | S | Q | E | L | K |

| | | | | | | | | | | | | | | | | | | | | |
|---|---|---|---|---|---|---|---|---|---|---|---|---|---|---|---|---|---|---|---|---|
| HXB2D | N | S | A | V | S | L | L | N | A | T | A | I | A | V | A | E | G | T | D | R |
| 133275 | N | S | A | I | S | L | L | N | A | T | A | I | A | V | A | E | G | T | D | R |
| 133276 | N | S | A | V | S | L | L | D | T | T | A | I | A | V | A | E | G | T | D | R |
| 133268 | N | S | A | V | S | L | Y | N | T | T | A | I | V | V | A | E | G | T | D | R |
| 142028 | T | S | A | V | N | L | L | N | A | T | A | I | A | V | A | E | G | T | D | R |

| | | | | | | | | | | | | | | | | | | | | |
|---|---|---|---|---|---|---|---|---|---|---|---|---|---|---|---|---|---|---|---|---|
| HXB2D | V | I | E | V | V | Q | G | A | C | R | A | I | R | H | I | P | R | R | I | R |
| 133275 | V | I | E | I | L | Q | R | I | F | R | A | V | I | H | V | P | R | R | I | R |
| 133276 | I | I | E | I | A | Q | R | V | F | R | A | F | L | H | I | P | R | R | I | R |
| 133268 | V | I | E | V | V | Q | R | A | C | R | A | I | Y | H | I | P | R | R | I | R |
| 142028 | V | I | E | V | V | Q | R | A | Y | R | A | L | L | H | I | P | T | R | I | R |

METHODS AND MEANS FOR ASSESSING HIV ENVELOPE INHIBITOR THERAPY

The present invention relates to methods and means for the evaluation of HIV treatment. In particular, molecular events at the HIV envelope protein and their effect on therapeutic efficacy of drugs are determined. The methods rely on providing HIV envelope nucleic acid material and evaluating a treatment either through genotyping or phenotyping. Said method may find use in multiple fields including diagnostics, drug screening, pharmacogenetics and drug development.

A number of different therapeutic regimens have been developed to treat HIV (human immunodeficiency virus) infection. However, like many viruses, HIV has no proofreading capacity, thus, it can quickly mutate to overcome the effects of drugs or combinations thereof targeted against it. Under the selective pressure of a given therapy, the virus mutates to phenotypes that reduce or eliminate the effects of the administered drugs. Despite the development of new classes of anti-HIV drugs such as protease (pro) and reverse transcriptase (RT) inhibitors and complex drug regimens, drug resistance continues to increase. Further, drug-resistant virus strains can infect new individuals, gradually replacing more treatable strains in the infected population.

The ease with which HIV can mutate under the selective pressure of drug therapy requires the frequent monitoring of the replicative capacity of a patient's virus in response to the patient's current therapy so that the therapeutic strategy can be adjusted or changed to provide maximum benefit over time. Often, the physician must change the doses of drugs, or initiate combination therapy using protease and reverse transcriptase inhibitors, or other types of anti-HIV drugs.

Accurate determination of the susceptibility of a patient's virus strain toward a variety of drugs or drug combinations is especially helpful in making decisions about appropriate treatment. In order to reduce drug resistance and assist physicians in choosing the best therapy for a given HIV-infected patient, sophisticated patient monitoring techniques have been developed, such as Antivirogram® (described in WO 97/27480 and U.S. Pat. No. 6,221,578 B1; incorporated herein by reference) and Phenosense™ (WO97/27319). These assays determine the resistance of patient borne virus towards a defined drug regimen by providing information about the susceptibility of the patient's virus strain to protease and reverse transcriptase inhibitors treatment. Many of the developed strategies use either immunologic means or sequencing techniques. The Antivirogram® and Genseq™ assays determine the phenotype and genotype respectively of a patient's reverse transcriptase and protease genes. The relevant coding regions are obtained from patient samples, reverse transcribed, and amplified by the polymerase chain reaction (PCR), then inserted into a plasmid to create chimeric viruses. The ability of these viruses to invade and kill cells in culture is assessed in the presence of HIV reverse transcriptase and protease inhibitors.

As resistance to current treatments grows, novel types of inhibitors are being developed focusing on other targets essential for viral replication and proliferation. These include inhibitors of the HIV envelope (env), tat, rev, integrase (IN), and other viral gene products. In the development of new drugs to suppress HIV replication, inhibitors of CD4 binding or chemokine receptor binding, and inhibitors of virus-cell membrane fusion, that target the envelope protein are promising candidates.

The HIV envelope is a glycoprotein consisting of two non-covalently associated subunits, gp120 and gp41, generated by proteolytic cleavage of the precursor gp160 protein, produced from the env gene on the HIV chromosome. This glycoprotein plays a critical role in the infection of cells. The gp120 subunit is involved in target cell recognition, while the gp41 subunit promotes fusion between the viral and cell membranes, allowing the virus to infect new cells. Examples of compounds designed to target the envelope glycoprotein are the entry inhibitors, such as T-20, T-1249, PRO-542, PRO-140, PRO-367, AMD-3100. Other entry inhibitors include AMD-070, SCH-C, SCH-D, and BMS-806. The clinical efficacy of these compounds is currently under investigation.

Despite the introduction of new anti-HIV drugs like those that target the envelope glycoprotein, new resistance mutations will inevitably arise. The envelope region is the most variable region of the HIV genome (i.e. highest frequency of mutations), providing numerous escape mutants to either drugs or neutralizing antibodies. Therefore, monitoring protocols to test the susceptibility of patient borne virus to envelope protein targeted drugs are needed. The present invention provides the means for phenotypic and genotypic evaluation of the drug efficacy of envelope inhibitors based on the analysis of patient borne viral strains. Assays for evaluating the wild-type or mutant HIV envelope are disclosed, using a set of primers designed for the retrieval, preparation and analysis of HIV genetic material.

Thus, the present invention relates to a method for determining the susceptibility of at least one human immunodeficiency virus to at least one drug, comprising:

i) obtaining at least one sample comprising HIV RNA or DNA, wherein the sample comprises at least one env gene or a portion thereof;

ii) reverse-transcribing and amplifying the HIV RNA, or amplifying the HIV DNA, with primers specific for env region of the HIV genome, to obtain at least one amplicon comprising the at least one env gene or a portion thereof;

iii) homologously recombining or ligating the at least one amplicon with the at least one plasmid comprising the wild-type HIV sequence with a deletion in the env region of the HIV genome, to prepare at least one recombinant virus; and iv) monitoring the at least one recombinant virus in the presence of the at least one drug to determine the phenotypic susceptibility.

More in particular, the present invention concerns a method for determining the susceptibility of at least one human immunodeficiency virus to at least one drug, comprising:

i) obtaining at least one sample comprising HIV RNA or DNA, wherein the sample comprises at least one env gene or a portion thereof;

ii) reverse-transcribing and amplifying the HIV RNA, or amplifying the HIV DNA, with primers specific for env region of the HIV genome, to obtain at least one amplicon comprising the at least one env gene or a portion thereof;

iii) using nucleic acid amplification to generate at least one plasmid containing the wild-type HIV sequence with a deletion in the env region of the HIV genome;

iv) homologously recombining or ligating the at least one amplicon with the at least one plasmid comprising the wild-type HIV sequence with a deletion in the env region of the HIV genome, to prepare at least one recombinant virus; and v) monitoring the at least one recombinant virus in the presence of the at least one drug to determine the phenotypic susceptibility.

Primers specific for amplification of HIV DNA env region or portions thereof include SEQ. ID 1-23, 40-47.

Primers useful for the amplification of the wild-type HIV sequence include SEQ. ID 32-34, 37-39. Optionally the primers may incorporate a restriction site, such as primers SEQ. ID 33, 34 and 38. Suitably, deletion constructs may be prepared by re-introducing portions of the env gene into a plasmid where the env gene has been previously deleted by amplification. Primers for amplifying the regions of interest, for example, the gp120 sequence, include SEQ ID 35-36.

Primers useful for ligation of the amplicons with the plasmids comprising the wild-type HIV sequence with a deletion in the env region of the HIV genome include SEQ. ID 48-50.

TABLE 1

Primers for obtaining and preparing amplicons, plasmids and recombinant viruses

| OLIGO NAME | SEQ ID NO | LENGTH | MW | Tm | SEQUENCE (5'-3') |
|---|---|---|---|---|---|
| | | 3' env PRIMERS | | | |
| ENV3AA1003 | SEQ ID NO:1 | 26 | 7817.0 | 71.9 | ATTCTTTCCCTTACAGCAGGCCATCC |
| ENV3INN1 | SEQ ID NO:2 | 22 | 6604.1 | 66.5 | GCTCCTACTCCTTCTGCTGCTG |
| ENV3OUT1 | SEQ ID NO:3 | 26 | 8026.1 | 65.8 | CTTAAAGGTACCTGAGGTCTGACTGG |
| ENV3INN2 | SEQ ID NO:4 | 24 | 7439.7 | 69.4 | GGTGTGTAGTTCTGCCAATCAGGG |
| ENV3OUT2 | SEQ ID NO:5 | 28 | 8517.5 | 70.7 | CAACTGGTACTAGCTTGAAGCACCATCC |
| | | 5' env (gp 160) PRIMERS | | | |
| ENV5OUT1 | SEQ ID NO:6 | 27 | 8212.3 | 67.5 | CCTAAAGCCATGTGTAAAGTTAACCCC |
| ENV5INN1 | SEQ ID NO:7 | 24 | 7321.7 | 69.1 | CCATTACACAGGCTTGTCCAAAGG |
| ENV5AA1001 | SEQ ID NO:8 | 26 | 8089.2 | 64.1 | GCATGAGGATATAATCAGTTTATGGG |
| ENV5AA1002 | SEQ ID NO:9 | 26 | 7914.1 | 63.9 | TGTAATACCTCAGTCATTACACAGGC |
| 5'EGENV1 | SEQ ID NO:10 | 27 | 8341.4 | 70.6 | GGGATCAAAGCCTAAAGCCATGTGTAA |
| ENV5OUTA | SEQ ID NO:11 | 26 | 8413.4 | 73.6 | TGGGTACCTGTGTGGAAAGAAGCAAC |
| ENV5OUTC | SEQ ID NO:12 | 25 | 7648.9 | 73.7 | GTTTGGGCCACACATGCCTGTGTAC |
| ENV5OUTD | SEQ ID NO:13 | 25 | 7555.9 | 71.5 | CACACATGCCTGTGTACCCACAGAC |
| ENV5OUTE | SEQ ID NO:14 | 27 | 8286.4 | 70.6 | GTGTGGAAAGAAGCAACCACCACTCTA |
| ENV5OUTF | SEQ ID NO:15 | 26 | 8057.1 | 66.1 | GTGGGTCACAGTCTATTATGGGGTAC |
| ENV5OUTG | SEQ ID NO:16 | 26 | 7856.1 | 73.0 | CCACAGACCCCAACCCACAAGAAGTA |
| ENV5OUTH | SEQ ID NO:17 | 27 | 8308.3 | 70.3 | CAGAGGTACATAATGTTTGGGCCACAC |
| | | 5' gp41 PRIMERS | | | |
| 5FAROUTgp41 | SEQ ID NO:18 | 23 | 7090.1 | 66.3 | CCTCAGGAGGGGACCYAGAAATT |
| 5OUTgp41 | SEQ ID NO:19 | 26 | 7912.1 | 72.3 | GGAMAAGCAATGTATGCCCCTCCCAT |
| 5INNgp41A | SEQ ID NO:20 | 24 | 7441.1 | 64.6 | CTTCAGACCTGGAGGAGGAGATAT |
| 5INNgp41B | SEQ ID NO:21 | 25 | 7868.1 | 66.9 | GGAGATATGAGGGACAATTGGAGAA |
| 5INNgp41C | SEQ ID NO:22 | 25 | 7845.1 | 71.0 | CCTGGAGGAGGAGATATGAGGGACA |
| 5INNgp41D | SEQ ID NO:23 | 21 | 6360.1 | 64.4 | CCATTAGGAGTAGCACCCACC |
| | | 5' rev-env PRIMERS | | | |
| 5LMENV1 | SEQ ID NO:40 | 24 | 7440.7 | 63.8 | TTGGGTGTCAACATAGCAGAATAG |
| 5LMENV2 | SEQ ID NO:41 | 24 | 7338.6 | 60.2 | CTGTTTATTCATTTTCAGAATTGG |
| 5LMENV3 | SEQ ID NO:42 | 25 | 7735.9 | 62.3 | CTATGAAACTTATGGGGATACTTGG |
| 5LMENV4 | SEQ ID NO:43 | 23 | 7032.5 | 65.9 | GCTCCATGGCTTAGGACAACATA |

TABLE 1-continued

Primers for obtaining and preparing amplicons, plasmids and recombinant viruses

| OLIGO NAME | SEQ ID NO | LENGTH | MW | Tm | SEQUENCE (5'-3') |
|---|---|---|---|---|---|
| | | 5' tat-rev-env PRIMERS | | | |
| 5LMENV5 | SEQ ID NO:44 | 24 | 7336.7 | 65.2 | AGATAAAGCCACCTTTGCCTAGTG |
| 5LMENV6 | SEQ ID NO:45 | 24 | 7369.7 | 56.5 | GACATAACAAGGTAGGATCTCTAC |
| 5LMENV7 | SEQ ID NO:46 | 24 | 7427.8 | 62.1 | ATCAAGCAGGACATAACAAGGTAG |
| 5LMENV8 | SEQ ID NO:47 | 21 | 6374.1 | 58.8 | GCAGACCAACTAATTCATCTG |
| | | MUTAGENESIS PRIMERS | | | |
| Env1 | SEQ ID NO:32 | 26 | — | — | GGGAATTGGCTCAAAGGATACCTTTGG |
| Env2 | SEQ ID NO:33 | 30 | — | — | GGGATCCTGCAGCCCGGGCTTGGAAAGGCC |
| Env6 | SEQ ID NO:34 | 23 | — | — | GGGTGCTACTCCTAATGGTTCAAT |
| Env3 | SEQ ID NO:37 | 27 | 8571.4 | 69.5 | GGGCTCTAGTCTAGGATCTACTGGCTCC |
| Env5 | SEQ ID NO:38 | 36 | 11175;<br>0 | 86.2 | GGATCCTGCAGCCCGGGTGGCAAGTGGTCAAAAACT |
| Env4 | SEQ ID NO:39 | 28 | 8537.3 | 73.3 | GGGGCTTGTTCCATCTATCCTCTGTCAG |
| | | WILD-TYPE CLONING PRIMERS | | | |
| C120-WT1 | SEQ ID NO:35 | 23 | — | — | ATACATTATTGTGCCCCGGCTGG |
| C120-WT2 | SEQ ID NO: 36 | 21 | — | — | GGGTGCTACTCCTAATGGTTC |
| | | gp41 CLONING PRIMERS | | | |
| 5CP41-P | SEQ ID NO:48 | 24 | 7588.9 | 68.4 | P-ACCAAGGCAAAGAGAAGAGTGGTG |
| 3CP41-P | SEQ ID NO:49 | 26 | 8081.0 | 61.1 | P-TGTCTTATTCTTCTAGGTATGTGGMG |
| 5CPenv-P | SEQ ID NO:50 | 22 | 6781.2 | 68.4 | P-ATACATTATTGTGCCCCGGCTG |

The invention relates to the plasmids described in the experimental part and to the use of the plasmids in the methods disclosed herein. The complete HIV sequence may be incorporated in the plasmid or only part(s) thereof, such as, for example, the plasmids used in the present invention may lack the gp41 portion of the env gene, or may additionally lack the gp120 portion. The invention also provides a plasmid comprising a HIV env deletion construct, wherein at least 100 base pairs (bp) of the HIV envelope gene are deleted, suitably wherein at least 250 bp of the HIV envelope gene are deleted, more suitably wherein at least 500 bp of the HIV envelope gene are deleted. The deletion may also comprise parts of flanking genes, or eventually more than one gene, e.g. deletion of env and rev, deletion of env, rev and tat. A suitable plasmid backbone may be selected from the group including pUC, pBR322 and pGEM.

The plasmids pSV40HXB2D Tat-Rev-Env (accession number LMBP 4570), pSV40HXB2D Rev Env (accession number LMBP 4569), pSV40HXB2D gp41 (accession number LMBP 4567), pSV40HXB2D Env (accession number LMBP 4571), pGEMHIV GPRT (accession number LMBP 4568) were deposited at the Belgian Coordinated Collections of Micro-Organisms located at the Universiteit Gent—Laboratorium voor Moleculaire Biologie on Jul. 1, 2002.

The methods for determining the susceptibility may be useful for designing a treatment regimen. For example, a method may comprise determining the relative replicative capacity of a clinical isolate of a patient and using said relative replicative capacity to determine an appropriate drug regimen for the patient.

The present invention also provides a method of identifying a drug effective against HIV envelope comprising: obtaining at least one HIV envelope sequence or a portion thereof, determining the phenotypic susceptibility of the envelope towards said drug, using said phenotypic susceptibility to determine the effectiveness of said drug.

In addition, the present invention relates as well to a kit for phenotyping HIV envelope gene. Such kit for determining the susceptibility of at least one HIV virus to at least one drug comprises: i) at least one of the primers selected from SEQ ID NO. 1-23 and 32-50; and ii) a plasmid as described in the present invention. For the purpose of performing the phenotyping assay, such kit may be further completed with at least one HIV inhibitor. Optionally, a reference plasmid bearing a wild type HIV sequence may be added. Optionally, cells susceptible of HIV transfection may be added to the kit. In addition, at least one reagent for monitoring the indicator genes or reporter molecules such as enzyme substrates may be added.

The invention further comprises a method for determining the susceptibility of at least one human immunodeficiency virus to at least one drug, comprising:

i) obtaining at least one sample comprising HIV RNA or DNA, wherein the sample comprises at least one env gene or a portion thereof;

ii) reverse-transcribing and amplifying the HIV RNA, or amplifying the HIV DNA, with primers specific for the env region of the HIV genome, to obtain at least one amplicon comprising the env gene or a portion thereof;

iii) determining the nucleotide sequence of the at least one amplicon or a portion thereof; and iv) comparing the nucleotide sequence of the at least one amplicon or portion thereof to the sequence of known sequences, to determine the susceptibility.

Primers useful for determining the nucleotide sequence of the amplicon or a portion thereof include SEQ. 24-31 and 51-57. This particular selection has the advantage that it enables the sequencing of the complete HIV envelope gene. Consequently, using this set of primers all possible mutations that may occur in the HIV envelope gene may be resolved.

cloning into a suitable vector. A variety of commercial sequencing enzymes and equipment may be used in this process. The efficiency may be increased by determining the sequence of the env-coding region in several parallel reactions, each with a different set of primers. Such a process could be performed at high throughput on a multiple-well plate, for example. Commercially available detection and analysis systems may be used to determine and store the sequence information for later analysis. The nucleotide sequence may be obtained using several approaches including sequencing nucleic acids. This sequencing may be performed using techniques including gel based approaches, mass spectroscopy and hybridization. However, as more resistance related mutations are identified, the sequence at particular nucleic acids, codons, or short sequences may be obtained. If a particular resistance associated mutation is known, the nucleotide sequence may be determined using hybridization assays (including Biochips, LipA-assay), mass spectroscopy, allele specific PCR, or using probes or primers discriminating between mutant and wild-type sequence. For these purposes the probes or primers may be suitably labeled for detection (e.g. Molecular beacons, TaqMan®, SunRise primers).

TABLE 2

Primers for sequencing the gp41 and g120 regions

| OLIGO NAME | SEQ ID NO | LENGTH | MW | Tm | SEQUENCE (5'-3') |
|---|---|---|---|---|---|
| | | gp41 SEQUENCING PRIMERS | | | |
| EnvSeq1 | SEQ ID NO:24 | 18 | 5941.6 | | GGGACAATTGGAGAAGTG |
| EnvSeq2 | SEQ ID NO:25 | 19 | 6161.8 | | GAATCGCAGAACCAGCAGG |
| EnvSeq4 | SEQ ID NO:26 | 20 | 6305 | | CCAATTCCACAGACTTGCCC |
| EnvSeq5 | SEQ ID NO:27 | 21 | 6772.2 | | GCTCCAGGCAAGAGTCCTGGC |
| EnvSeq6 | SEQ ID NO:28 | 22 | 7141.4 | | GAGTTAGGCAGGGATACTCACC |
| EnvSeq7 | SEQ ID NO:29 | 18 | 5576.6 | | CTCTCCACCTTCTTCTTC |
| EnvSeq8 | SEQ ID NO:30 | 26 | 8381.2 | | GCAGATGAGTTTTCCAGAGCAGCCCC |
| EnvSeq9 | SEQ ID NO:31 | 20 | 6302 | | CTTTTTGACCACTTGCCACC |
| | | gp120 SEQUENCING PRIMERS | | | |
| gp120f_seq1 | SEQ ID NO:51 | 18 | 5534 | 54 | ATGCTCCTTGGGATGTTG |
| gp120f_seq2 | SEQ ID NO:52 | 18 | 5432 | 54 | AACCCCACTCTGTGTTAG |
| gp120f_seq3 | SEQ ID NO:53 | 20 | 5985 | 60 | CCCATACATTATTGTGCCCC |
| gp120f_seq4 | SEQ ID NO:54 | 18 | 5638 | 52 | GTTTTAATTGTGGAGGGG |
| gp120r_seq5 | SEQ ID NO:55 | 18 | 5391 | 60 | GTGCTTCCTGCTGCTCCC |
| gp120r_seq6 | SEQ ID NO:56 | 18 | 5438 | 52 | GGCATACATTGCTTTTCC |
| gp120r_seq7 | SEQ ID NO:57 | 20 | 6243 | 60 | GGGGCACAATAATGTATGGG |

The present invention also relates to a kit for genotyping HIV envelope gene. Such kit useful for determining the susceptibility of at least one HIV virus to at least one drug comprises at least one of the primers selected from SEQ ID NO. 1-31, 40-47 and 51-57. Optionally, additional reagents for performing the nucleic amplification and subsequent sequence analysis may be added. Reagents for cycle sequencing may be included. The primers may be fluorescently labeled.

The genotype of the patient-derived env coding region may be determined directly from the amplified DNA by performing DNA sequencing during the amplification step. Alternatively, the sequence may be obtained after sub- A viral sequence may contain one or multiple mutations versus consensus wild-type. A single mutation or a combination of env mutations may correlate to a change in drug efficacy. This correlation may be indicative of reduced or increased susceptibility of the virus for a drug. Said mutations may also influence the viral fitness. Mutations in the patient borne HIV env may be identified by sequence comparison with a reference sequence of a viral strain e.g. K03455. K03455 is present in Genbank and available through the internet. The identified mutation may be indicative of a change in susceptibility of the viral strain for one or more drugs. Said susceptibility data are derived from phenotypic analysis, wherein the env sequence comprising said mutation is analyzed. For example, resistance mutations to compound AMD-3100 include amongst others, Q278T, I288T, and N293D in gp120. Examples of resistance mutations to compound T-20 in the gp41 are G36S, V38M.

The present invention further provides a method of identifying a drug effective against HIV envelope comprising: obtaining at least one HIV envelope sequence or a portion thereof, determining the sequence of the HIV envelope, comparing said sequence with sequences present in a database, of which the phenotypic susceptibility has been determined with the methods of the present invention, using said sequence comparison to determine the effectiveness of said drug.

Results from phenotyping and genotyping experiments can be used to develop a database of replicative capacity levels in the presence of particular drugs, drug regimens or other treatment for a large number of mutant HIV strains. One such approach is virtual phenotyping (WO 01/79540). Briefly, the genotype of a patient derived env sequence may be correlated to the phenotypic susceptibility of said patient derived env sequence. If no phenotyping is performed, the sequence may be screened towards a collection of sequences present in a database. Identical sequences are retrieved and the database is further interrogated to identify if a corresponding phenotype is known for any of the retrieved sequences. In this latter case a virtual phenotype may be determined (see also infra). A report may be prepared including the $EC_{50}$ of the viral strain for one or more therapies, the sequence of the strain under investigation, biological cut-offs. Suitably, complete sequences will be interrogated in the database. Optionally, portions of sequences, such as combinations of mutations indicative of a change in drug susceptibility, may as well be screened. Such combination of mutations is sometimes referred to as a hot-spot (see e.g. WO 01/79540). Additionally, data may then be incorporated into existing programs that analyze the drug susceptibility of viruses with mutations in other segments of the HIV genome such as in the pol genes. For example, such a database may be analyzed in combination with reverse transcriptase and protease sequence information and the results used in the determination of appropriate treatment strategies.

As such, the invention concerns a method of constructing a genotypic and phenotypic database of env sequences or portions thereof, comprising:

i) obtaining samples comprising HIV RNA or DNA, wherein the samples comprise the env gene or portions thereof;
ii) reverse-transcribing and amplifying the HIV RNA, or amplifying the HIV DNA, with primers specific for the env region of the HIV genome, to obtain amplicons comprising the env gene or portions thereof;
iii) determining the nucleotide sequence of the amplicons or portions thereof;
iv) homologously recombining or ligating the amplicons with the plasmids comprising the wild-type HIV sequence with a deletion in the env region of the HIV genome, to prepare recombinant viruses; and
v) determining the replicative capacity of the recombinant viruses in the presence of anti-HIV drugs by comparing the replicative capacity of the recombinant HIV viruses with the replicative capacity of a wild-type env gene sequence;
vi) correlating the nucleotide sequence and relative replicative capacity in a data table.

More in particular, the invention concerns a method of constructing a genotypic and phenotypic database of env sequences or portions thereof, comprising:

i) obtaining samples comprising HIV RNA or DNA wherein the samples comprise the env gene or portions thereof;
ii) reverse-transcribing and amplifying the HIV RNA, or amplifying the HIV DNA, with primers specific for the env region of the HIV genome, to obtain amplicons comprising the env gene or portions thereof;
iii) determining the nucleotide sequence of the amplicons or portions thereof;
iv) using nucleic acid amplification to generate plasmids containing the wild-type HIV sequence with a deletion in the env region of the HIV genome;
v) homologously recombining or ligating the amplicons with the plasmids comprising the wild-type HIV sequence with a deletion in the env region of the HIV genome, to prepare recombinant viruses;
vi) determining the replicative capacity of the recombinant viruses in the presence of anti-HIV drugs by comparing the replicative capacity of the recombinant HIV viruses with the replicative capacity of a wild-type env gene sequence; and
vii) correlating the nucleotide sequence and relative replicative capacity in a data table.

Thus, obtained phenotypic and genotypic data enable the development of a database comprising both phenotypic and genotypic information of the HIV envelope, wherein the database further provides a correlation in between genotypes and genotypes, and in between genotypes and phenotypes, wherein the correlation is indicative of efficacy of a given treatment regimen. Such a database can further be used to predict the phenotype of a HIV envelope gene based on its genotypic profile.

A human immunodefieciency virus (HIV), as used herein refers to any HIV including laboratory strains, wild type strains, mutant strains and any biological sample comprising at least one HIV virus, such as, for example, an HIV clinical isolate. HIV strains compatible with the present invention are any such strains that are capable of infecting mammals, particularly humans. Examples are HIV-1 and HIV-2.

For reduction to practice of the present invention, an HIV virus refers to any sample comprising at least one HIV virus. Since a patient may have HIV viruses in his body with different mutations in the env gene, it is to be understood that a sample may contain a variety of different HIV viruses containing different mutational profiles in the env gene. A sample may be obtained for example from an individual, from cell cultures, or generated using recombinant technology, or cloning.

HIV strains compatible with the present invention are any such strains that are capable of infecting mammals, particularly humans. Viral strains used for obtaining a plasmid are preferably HIV wild-type sequences, such as LAI, HXB2D. LAI, also known as IIIB, is a wild-type HIV strain. One particular clone thereof, this means one sequence, is HXB2D. This sequence may be incorporated into a plasmid.

Instead of viral RNA, HIV DNA, e.g. proviral DNA, may be used for the methods described herein. In case RNA is used, reverse transcription into DNA by a suitable reverse transcriptase is needed. The protocols describing the analysis of RNA are also amenable for DNA analysis. However, if a protocol starts from DNA, the person skilled in the art will know that no reverse transcription is needed. The primers designed to amplify the RNA strand, also anneal to, and amplify DNA. Reverse transcription and amplification may be performed with a single set of primers. Suitably a hemi-nested and more suitably a nested approach may also be used to reverse transcribe and amplify the genetic material.

Nucleic acid may be amplified by techniques such as polymerase chain reaction (PCR), nucleic acid sequence based amplification (NASBA), self-sustained sequence replication (3SR), transcription-based amplification (TAS), ligation chain reaction (LCR). Often PCR is used.

For the purpose of the present invention an amplicon refers to the amplified and, where necessary, reverse-transcribed env gene or portions thereof. Additionally, the amplicon may include the flanking regions of the envelope gene, such as the tat and rev sequences, or portions thereof. It should be understood that this env gene may be of diverse origin, including plasmids and patient material; suitably it is obtained from patient derived material. Amplicon is sometimes defined as the "DNA construct". A portion of the env gene is defined as a fragment of env gene recovered from patient borne virus, lab viruses including IIIB and NL4-3, or mutant viruses. This fragment does not encompass the complete env. Said fragment may be obtained directly from its source, including a patient sample, or may be obtained using molecular biology tools following the recovery of the complete env sequence.

It may not be necessary to amplify the entire env gene in the context of the present invention to determine the susceptibility of an HIV isolate to anti-HIV drugs. For example, current HIV envelope glycoprotein inhibitors such as T-20 and T-1249 interact with the gp41 subunit of the envelope. Therefore, it is likely that resistance associated mutations to these compounds will mainly arise in the gp41 subunit. If this is the case, it may be sufficient to amplify only the gp41 region of the env gene for use in phenotyping and genotyping.

Primers specific for the env region of the HIV genome such as the primers described herein and their homologs are claimed. Such primers are chosen from SEQ. ID N° 1-57 or have at least 80% homology, preferably 90% homology, more preferably 95% homology as determined using algorithms known to the person skilled in the art such as FASTA and BLAST. Interesting sets of primers include at least one primer selected from SEQ. ID N° 1-50. The primer sequences listed herein may be labeled. Suitably, this label may be detected using fluorescence, luminescence or absorbance. In addition primers located in a region of 50 nucleotides (nt) upstream or downstream from the sequences given herein constitute part of the present invention. Specifically, the primers may be located in a region of 20 nt upstream or downstream from the sequences given herein and, constitute, as well, part of the present invention. Also, primers comprising at least 8 consecutive bases present in either of the primers described herein constitute an embodiment of the invention. Interestingly, the primers comprise at least 12 consecutive bases present in either of the primers described herein. In one aspect of the present invention the primers may contain linker regions for cloning. Optionally, the linker region of a primer may contain a restriction enzyme recognition site. Preferably, said restriction enzyme recognition site is a unique restriction enzyme recognition site. Alternatively, primers may partially anneal to the target region.

A drug means any agent such as a chemotherapeutic, peptide, antibody, antisense, ribozyme and any combination thereof be it marketed or under development. Examples of drugs include protease inhibitors including ritonavir, amprenavir, nelfinavir; reverse transcriptase inhibitors such as nevirapine, delavirdine, AZT, zidovudine, didanosine; envelope inhibitors; integrase inhibitors. In particular, agents interfering with HIV envelope biology are analyzed. Treatment or treatment regimen refers to the management or handling of an individual medical condition by the administration of drugs, at directed dosages, time intervals, duration, alone or in different combinations, via different administration routes, in suitable formulations, etc.

The susceptibility of at least one HIV virus to at least one drug is determined by the replicative capacity of the recombinant virus in the presence of at least one drug relative to the replicative capacity of an HIV virus with a wild-type env gene sequence in the presence of the same at least one drug. Replicative capacity means the ability of the virus or chimeric construct to grow under culturing conditions. This is sometimes referred to as viral fitness. The culturing conditions may contain triggers that influence the growth of the virus, examples of which are drugs.

An alteration in viral drug sensitivity is defined as a change in susceptibility of a viral strain to said drug. Susceptibilities are generally expressed as ratios of $EC_{50}$ or $EC_{90}$ values. The $EC_{50}$ or $EC_{90}$ value is the effective drug concentration at which 50% or 90% respectively of the viral population is inhibited from replicating. The $IC_{50}$ or $IC_{90}$ value is the drug concentration at which 50% or 90% respectively of the enzyme activity is inhibited. Hence, the susceptibility of a viral strain can be expressed as a fold change in susceptibility, wherein the fold change is derived from the ratio of, for instance, the $EC_{50}$ or $IC_{50}$ values of a mutant viral strain, compared to the wild type $EC_{50}$ or $IC_{50}$ values. In particular, the susceptibility of a viral strain or population may also be expressed as resistance of a viral strain, wherein the result is indicated as a fold increase in $EC_{50}$ or $IC_{50}$ as compared to wild type $EC_{50}$ or $IC_{50}$.

The susceptibility of at least one HIV virus to one drug may be tested by determining the cytopathogenicity of the recombinant virus to cells. In the context of this invention, the cytopathogenic effect means, the viability of the cells in culture in the presence of chimeric viruses. The cells may be chosen from T cells, monocytes, macrophages, dendritic cells, Langerhans cells, hematopoietic stem cells or, precursor cells, MT4 cells and PM-1 cells. Suitable host cells for homologous recombination of HIV sequences include MT4 and PM-1. MT4 is a $CD4^{+}$ T-cell line containing the CXCR4 co-receptor. The PM-1 cell line expresses both the CXCR4 and CCR5 co-receptors. All the above mentioned cells are capable of producing new infectious virus particles upon recombination of the env deletion vectors with the env amplicons. Thus, they can also be used for testing the cytopathogenic effects of recombinant viruses. The cytopathogenicity may, for example, be monitored by the presence of a reporter molecule including reporter genes. A reporter gene is defined as a gene which product has reporting capabilities. Suitable reporter molecules include tetrazolium salts, green fluorescent proteins, beta-galactosidase, chloramfenicol transferase, alkaline phosphatase, and luciferase. Several methods of cytopathogenic testing including phenotypic testing are described in the literature comprising the recombinant virus assay (Kellam and Larder, Antimicrob. Agents Chemotherap. 1994, 38, 23-30, Hertogs et al. Antimicrob. Agents Chemotherap. 1998, 42, 269-276; Pauwels et al. J. Virol Methods 1988, 20, 309-321).

The term chimeric means a construct comprising nucleic acid material from different origin such as, for example, a combination of wild type virus with a laboratory virus, a combination of wild type sequence and patient derived sequence.

The sequence to be specifically detected by sequence analysis according to the present invention may be a wild type, polymorphic or mutant sequence of the HIV env gene or fragment thereof. This nucleotide sequence may encompass one or several nucleotide changes. Target sequences may refer to single nucleotide positions, nucleotides encoding amino acids or to sequence spanning any of the foregoing nucleotide positions. In the present invention said sequence often includes one or two variable nucleotide positions. Sequence alterations detected by the present method include but are not limited to single nucleotide mutations, substitutions, deletions, insertions, transversions, inversions, repeats or variations covering multiple variations, optionally present at different locations. Sequence alterations may further relate to epigenetic sequence variations not limited to for instance methylation.

Any type of patient sample may be used to obtain the envelope gene, such as, for example, serum and tissue. Viral RNA may be isolated using known methods such as that described in Boom, R. et al. (J. Clin. Microbiol. 28(3): 495-503 (1990); incorporated herein by reference). Alternatively, a number of commercial methods such as the QIAAMP® viral RNA kit (Qiagen, Inc.) may be used to obtain viral RNA from bodily fluids such as plasma, serum, or cell-free fluids. DNA may be extracted from tissue using methods known by the skilled in the art such as the procedure described by Maniatis et al. (1982) which involves the preparation of a cell lysate followed by digestion with proteinase K, obtaining DNA purification by a multi-step phenol extraction, ethanol precipitation and ribonuclease digestion. Optionally, available commercial methods may also be employed to obtain DNA from bodily fluids, such as QIAAMP® Blood kits for DNA isolation from blood and body fluids (Qiagen, Inc.)

To prepare recombinant HIV viruses for phenotyping assays, the amplified sequences of gp41, gp120, env (gp160), rev-env, tat-rev-env, or portions thereof, also termed herein as amplicons, may be inserted into a vector comprising the wild-type HIV sequence with a deletion of the relevant portion. An infectious clone is generated upon exchange of genetic material between the amplicon and the deletion construct to yield an HIV sequence.

In the present invention, there is further disclosed a method for obtaining a plasmid containing the wild-type HIV sequence with a deletion in the env, tat, and/or rev regions of the HIV genome. The removal of the region of interest is achieved by amplification of a plasmid containing the wild type HIV sequence, such as HXB2D.

This plasmid amplification refers to the selective amplification of a portion of the plasmid using primers annealing to the flanking sequences of the desired deletion region, i.e. env sequence, such that all plasmid is amplified except for the region to be deleted. Such method of amplification is a direct, one-step, and simple technique to produce a deletion of a sequence in a circular plasmid DNA.

Preferably, said amplification of plasmid's DNA generates a unique restriction site. Unique restriction site refers to a single occurrence of a site on the nucleic acid that is recognized by a restriction enzyme or that it does not occur anywhere else in the construct. The unique restriction site may be created after amplification by re-ligating both 5' and 3' ends of the amplified plasmid's DNA. Alternatively, the unique restriction site may not have to be created, as it may be already fully located in one of the ends, 5' or 3' end. Optionally, the unique restriction site may be inserted. Optionally, part of the unique restriction site may be present in the region to be amplified. The creation of a unique restriction site deriving from amplification is a preferred method since is a one-step, direct, simple and fast method. The unique restriction site is further relevant for the production of recombinant virus.

As one skilled in the art will understand, the creation of a unique restriction site will depend upon the sequence of the HIV genome, and upon the sequence to be deleted therefrom. Unique restriction sites that can be employed in the present invention are those present only once in the HIV genome and may flank the region of interest to be deleted. Optionally, the primers used for amplification may contain the same or other specific restriction endonuclease sites to facilitate insertion into a different vector. Additionally, one of the primers used for amplification may contain a phosphorylated 5' end-linker to facilitate insertion of a foreign amplicon. One interesting unique restriction site is SmaI.

Optionally, the method for obtaining a plasmid containing the wild-type HIV sequence with a deletion in the env, tat, and/or rev regions of the HIV genome, may be performed in a second cloning vector. The env region may be inserted into a cloning vector such as pGEM (Promega, for example the backbone of pGEM3 vector has been used) and manipulated, by amplification, to remove part of the gp120 and/or gp41-coding region such that insertion of the remaining env sequence from the samples would not disrupt the reading frame. The manipulated env region is then placed in a pSV40HXB2D vector such that it contains the complete wild type HIV sequence except for the relevant gp41, gp120, or env deletions.

An example env deletion vector is pSV40HXB2D ENV, which has a deletion of 1904 base pairs of the env sequence comprising the entire gp41 coding region and a large portion of the gp120 coding region. The first 641 base pairs of the env coding sequence, including the v1 and v2 loops, remain. An example gp41 deletion vector is pSV40HXB2D gp41, which has a deletion of 1053 base pairs of the gp41 coding region.

Those of skill in the art will appreciate that other HIV vectors and cloning procedures known in the art may also be used to create gp41, gp120, env (gp160), rev-env, or tat-rev-env plasmids for recombination or ligation with patient derived sequences and creation of infectious viruses. For instance, deletion constructs may be prepared by re-introducing portions of the env gene into a plasmid wherein the env gene has been previously deleted by amplification. Primers for amplifying the regions of interest, the portions to be re-introduced, for example, the gp120 sequence, include SEQ ID 35-36. In general, vectors must be created to allow re-insertion of the deleted sequences without disrupting the reading frame of the tat, rev, or env genes.

The amplified env, gp120 or gp41 sequences may be inserted into the appropriate env, gp120 or gp41 vector by homologous recombination in a suitable host cell between overlapping DNA segments in the vector and amplified sequence. Alternatively, the amplified env, gp120 or gp41 sequence can be incorporated into the vector at a unique restriction site according to cloning procedures standard in the art. This latter is a direct cloning strategy. Suitable for direct cloning strategies are two different restriction sites are used to facilitate ligation of the amplified region in the appropriate orientation.

It may be convenient to insert gp120 and gp41 sections of the env gene into the vector even when mutations are only expected in one of these two sections. Recombinant viruses incorporating most or all of the env sequence would prevent incompatibility between mixed gp41 and gp120 subunits in a recombinant vector. Recombinant vectors bearing env subunits i.e. gp41 or gp120 or parts thereof from different origin could yield incompatibility upon transfecting cell lines. Recombinant virus stocks are stored for future analysis, such as for example, viability testing.

Following the generation of the recombinant construct the chimeric virus may be grown and the viral titer determined (expressed as multiplicity of infection, MOI) before proceeding to the determination of the phenotypic susceptibility. The indicator gene, encoding a signal indicative of replication of the virus in the presence of a drug or indicative of the susceptibility of the virus in the presence of a drug may be present in the culturing cells such as MT-4 cells. Alternatively, said indicator gene may be incorporated in the chimeric construct introduced into the culturing cells or may be introduced separately. Suitable indicator genes encode for fluorescent proteins, particularly green fluorescent protein or mutant thereof. In order to allow homologous recombination, genetic material may be introduced into the cells using a variety of techniques known in the art including, calcium phosphate precipitation, liposomes, viral infection, and electroporation. The monitoring may be performed in high throughput.

The protocols and products of the present invention may be used for diverse diagnostic, clinical, toxicological, research and forensic purposes including, drug discovery, designing patient therapy, drug efficacy testing, and patient management. The present methods may be used in combination with other assays. The results may be implemented in computer models and databases. The products described herein may be incorporated into kits.

Additionally, the protocols and products of the present invention also allow monitoring of the resistance profiles of anti-HIV compounds that target env gene products. They may also be useful in determining how the effectiveness of a variety of different types of anti-HIV compounds depends on env phenotype and genotype. Examples of anti-HIV drugs that can be tested in this assay include, nucleotide, nucleoside, and non-nucleoside reverse transcriptase inhibitors, protease inhibitors, entry inhibitors, and integrase inhibitors. Particularly, anti-HIV drugs that can be tested in this assay include entry inhibitors, which include membrane-fusion inhibitors, such as T-20, T-1249, PRO-542, PRO-140, PRO-367, AMD-3100, AMD-070, SCH-C, SCH-D, and BMS-806, but those of skill in the art will appreciate that other types of antiviral compounds may also be tested. Additionally, the activity of antivirals which target the env, tat, rev genes, may be screened by running clinically significant HIV strains encompassing mutant env, tat, rev sequences, wild-type env, tat, rev sequences, or optionally in the presence of neutralizing antibodies, chemokines, or plasma proteins, in a phenotypic assay. In a similar embodiment, the phenotypic assay may be used as or comprise part of a high-throughput screening assay where numerous antivirals and HIV strains compositions are evaluated. The results may be monitored by several approaches including but not limited to morphology screening, microscopy, and optical methods, such as, for example, absorbance and fluorescence.

The assays of the present invention may as well be used for therapeutic drug monitoring. Said approach includes a combination of susceptibility testing, determination of drug level and assessment of a threshold. Said threshold may be derived from population based pharmacokinetic modeling (WO 02/23186). The threshold is a drug concentration needed to obtain a beneficial therapeutic effect in vivo. The in vivo drug level may be determined using techniques such as high performance liquid chromatography, liquid chromatography, mass spectroscopy or combinations thereof. The susceptibility of the virus may be derived from phenotyping or interpretation of genotyping results.

In addition, the assays of the present invention may also be useful to discriminate an effective drug from an ineffective drug by establishing cut-offs, i.e. biological cut-offs (see e.g. WO 02/33402). Biological cut-offs are drug specific. These cut-offs are determined following phenotyping of a large population of individuals mainly containing wild-type viruses. The cut-off is derived from the distribution of the fold increase in resistances of the wild-type viruses for a particular drug.

BRIEF DESCRIPTION OF THE DRAWINGS

FIG. 8. Alignment ofgp41 amino acid sequences. HXB2D sequence is the reference HIV sequence (represented in SEQ ID NO: 58, amino acids 260-359). 133275, 133276, 133268 and 14028 are Virco IDs for individual gp41 sequences (represented in SEQ ID NO: 59, amino acids 261-360, SEQ ID NO: 60, amino acids 260-360, SEQ ID NO: 61, amino acids 261-360, and SEQ ID NO: 62, amino acids 260-359, respectively). Legend: amino acids (AA) are given in their one letter code, differences from HXB2D inpatient samples are marked in red, AA 36 to 38 from gp41 are marked in boldface to indicate the region of which specific polymorphisms were evaluated.

The following non-limiting examples help to illustrate the principles of the invention.

EXPERIMENTAL PART

Example 1

Design of Deletion Plasmids

A) Design of an Env (gp160) Deletion Plasmid

Figures 1A, 1B, 1C:
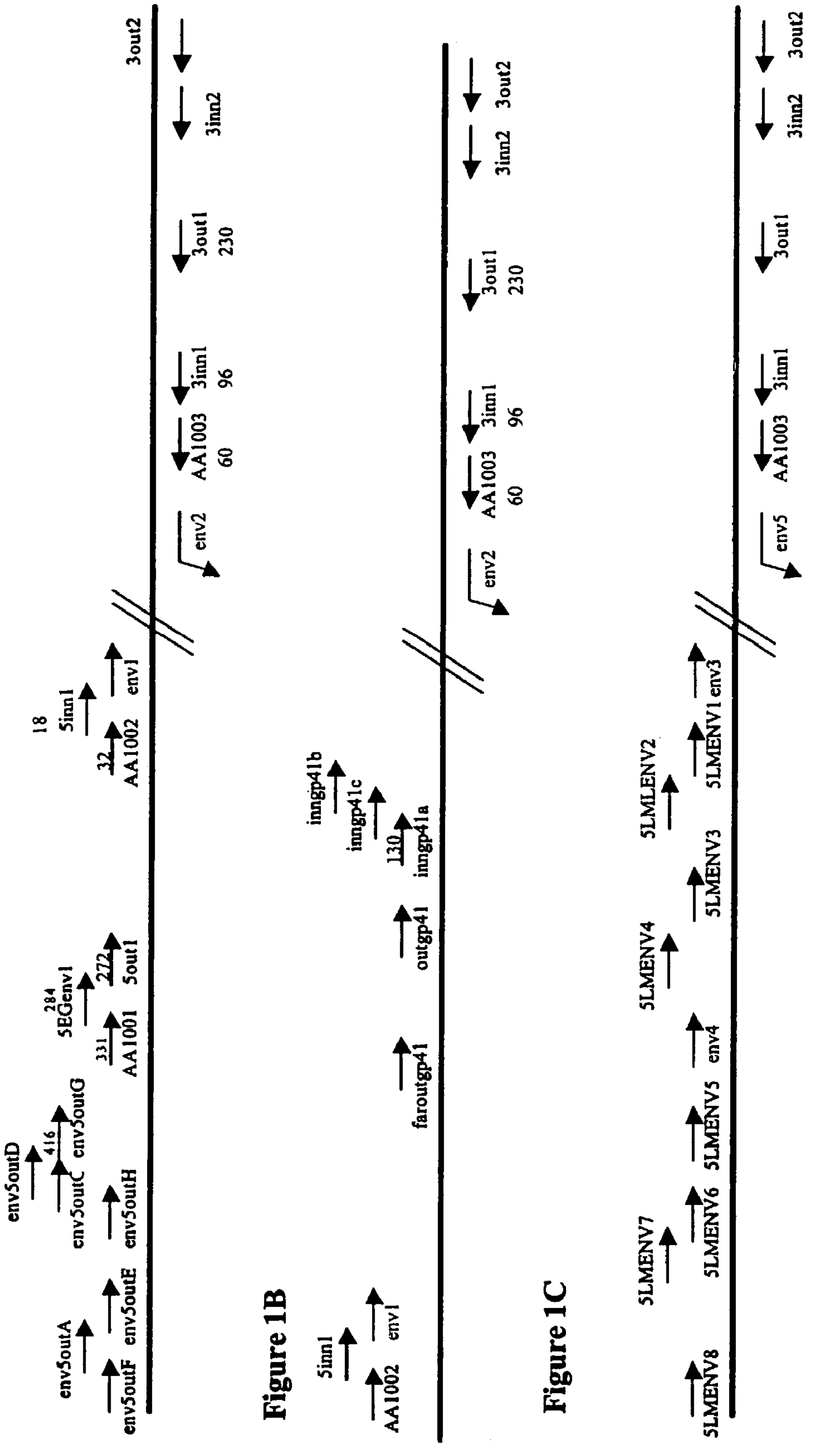
FIG. 1A. Overview env primers (full env).
FIG. 1B. Overview env primers (gp41 env assay).
FIG. 1C. Overview env primers (Tat-Rev-Env).
Figure 2:
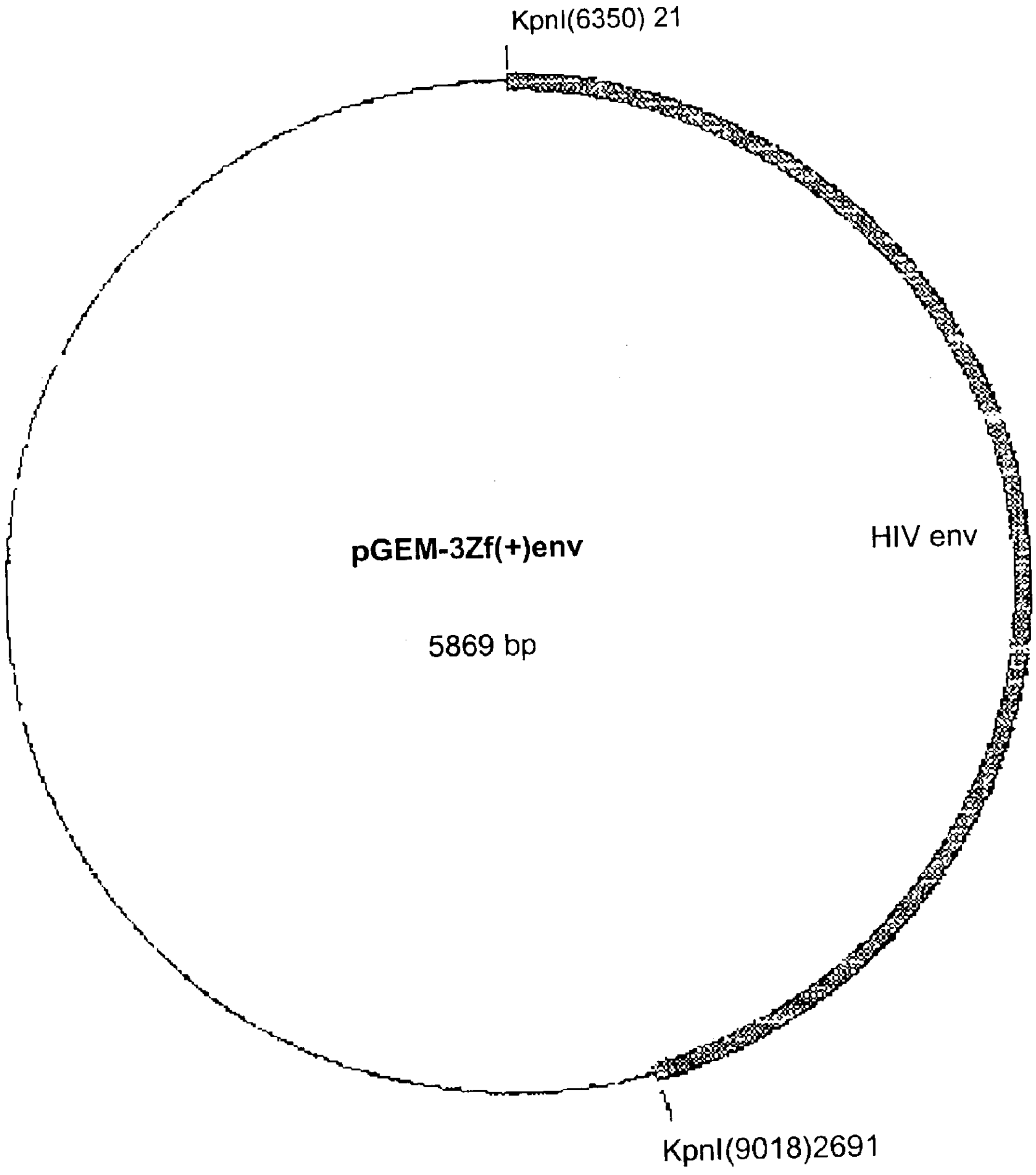
FIG. 2. Schematic representation of the pGEM vector containing the HIV env gene. The pGEM vector backbone is based on the pGEM3Zf(+) plasmid. The HIV env gene has been introduced into the KpnI site. The location of the HIV sequence is indicated in gray.
Figure 3:
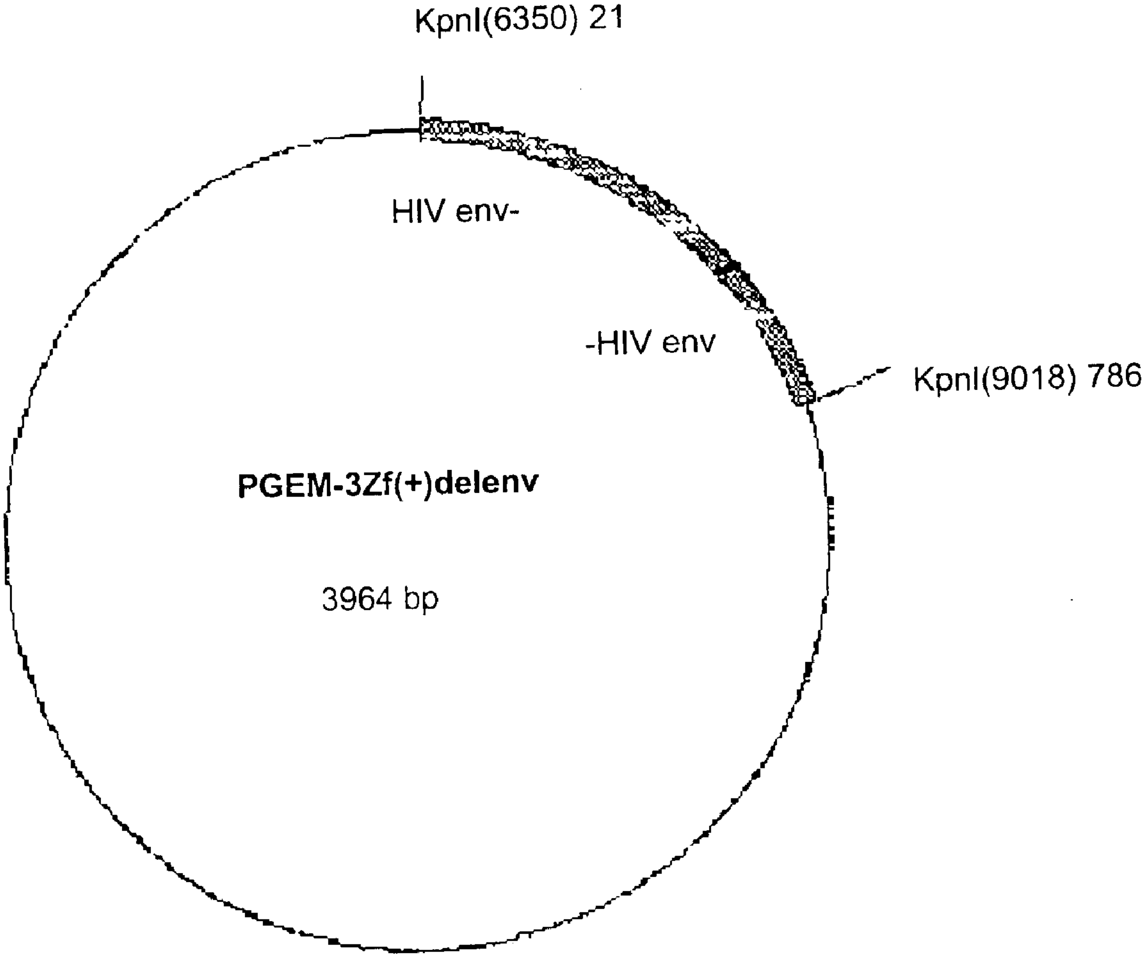
FIG. 3. Schematic representation of the pGEM env vector. The location of the HIV sequence is indicated in gray.
Figure 4:
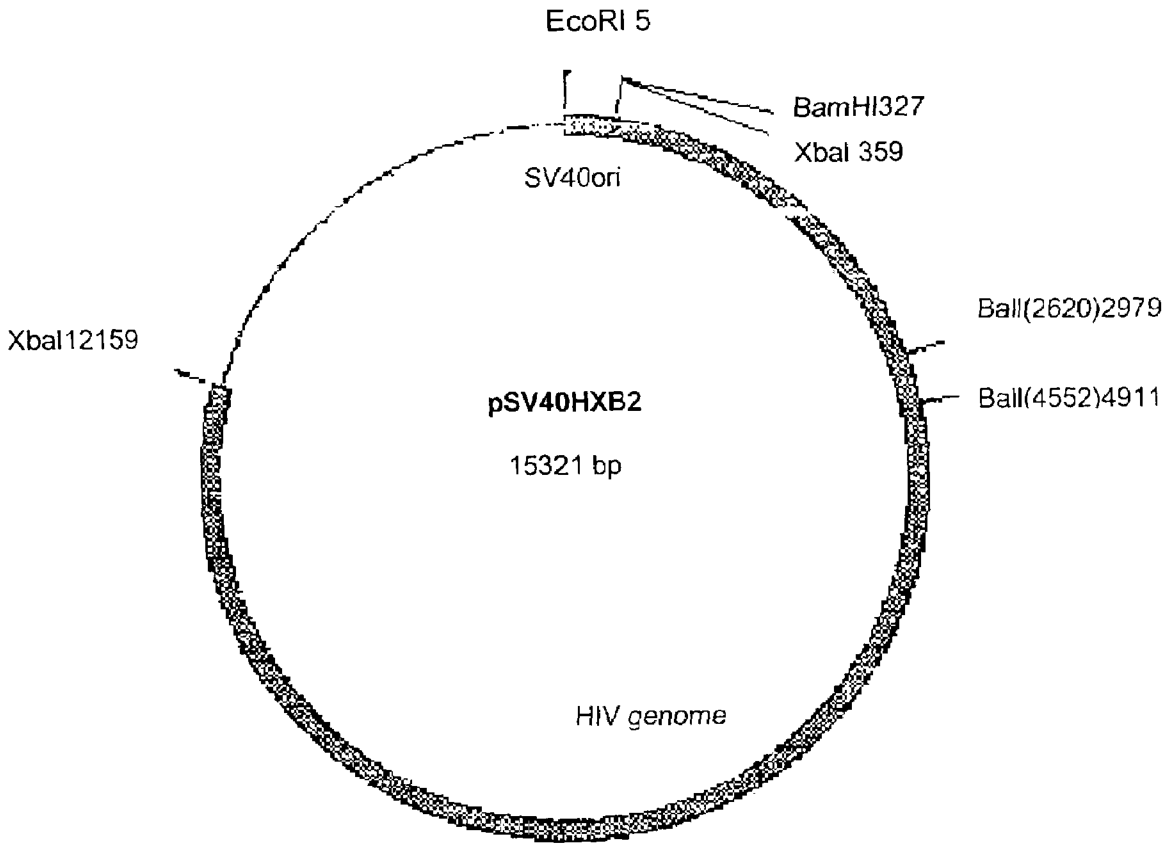
FIG. 4. Schematic representation of pSV40HXB2D vector. The location of the HIV sequence is indicated in gray.

To prepare a plasmid containing the wild type HIV sequence and a deletion in the env gene into which patient derived env DNA could be inserted, HIV env DNA was taken from the HXB2D GPRT vector and modified using a pGEM plasmid, then was inserted into a pSV40HXB2D infectious clone. Using KpnI restriction digestion, a 2668 bp fragment containing wild type env sequence was excised from the HXB2D GPRT vector. The fragment corresponded to nucleotides 6350-9018 of HXB2D GPRT. This fragment was introduced into the KpnI site of a pGEM vector to make pGEMENV, shown in FIG. 2. A 1905 base-pair fragment of the 2668 base-pair pGEMENV KpnI insert was then effectively deleted by amplification of the plasmid using oligos containing SmaI restriction sites (SEQ ID NO:32: 5' ggg aat tgg ctc aaa gga tac ctt tgg-3'; SEQ ID NO:33: 5'-ggg atc ctg cag ccc ggg ctt gga aag gcc-3'). These primers annealed to nucleotides 6386-6412 and 8317-8327 of the insert (numbering based on HIV reference sequence gi 9629357). The amplified DNA was cleaved with SmaI and religated to create the pGEM ENV plasmid, shown in FIG. 3. The 1905 base-pair deletion included all of the gp41 coding region and a major part of the gp120 coding region. The first 641 base pairs of the env gene remained, including the sequence coding for the v1 and v2 loops. The remaining KpnI fragment was then introduced into a pSV40HXB2D infectious clone, shown in FIG. 4.

Figure 5:
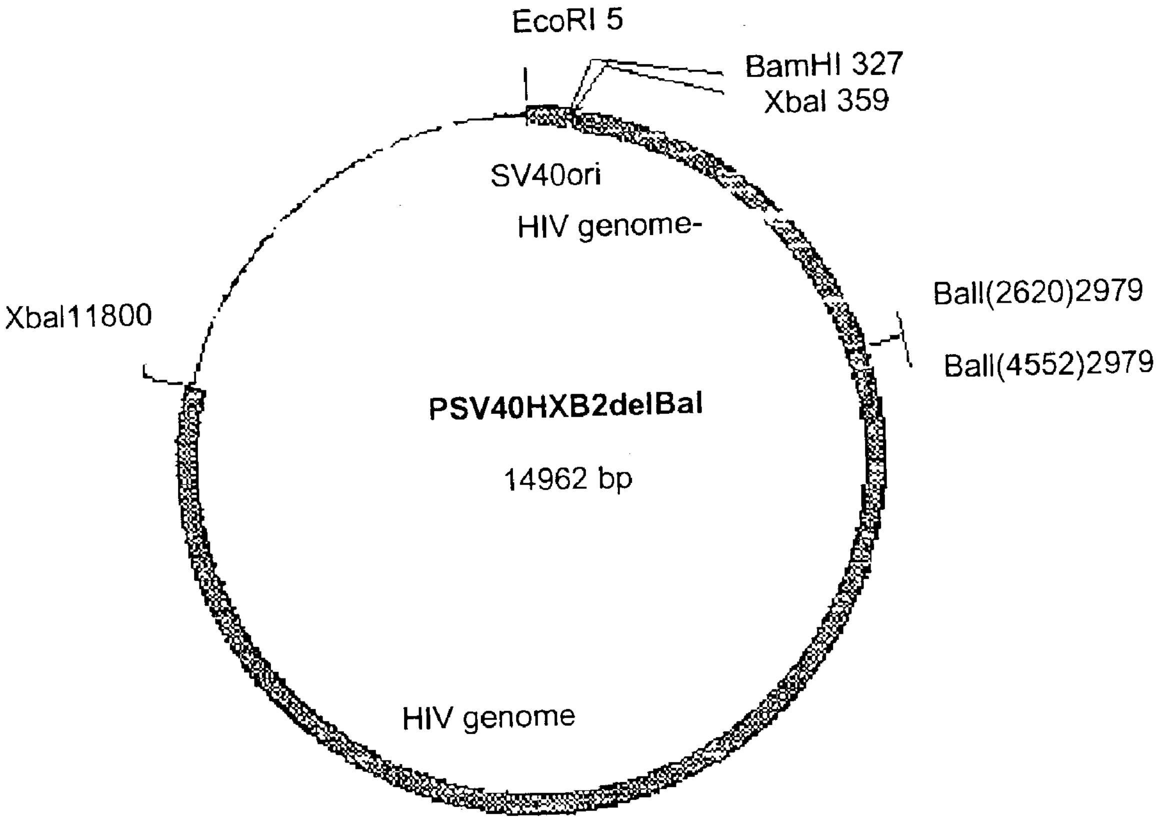
FIG. 5. Schematic representation of pSV40HXB2D Bal vector. The location of the HIV sequence is indicated in gray.
Figure 6:
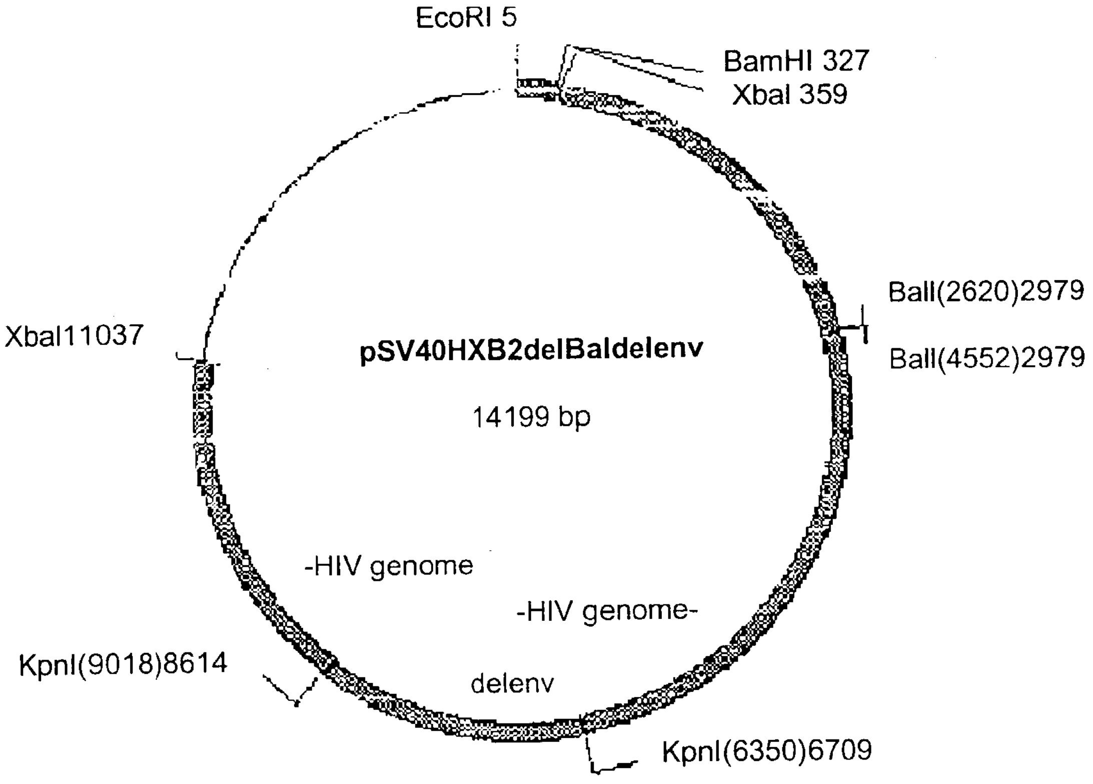
FIG. 6. Schematic representation of pSV40HXB2D Bal env vector. The location of the HIV sequence is indicated in gray.
Figure 7:
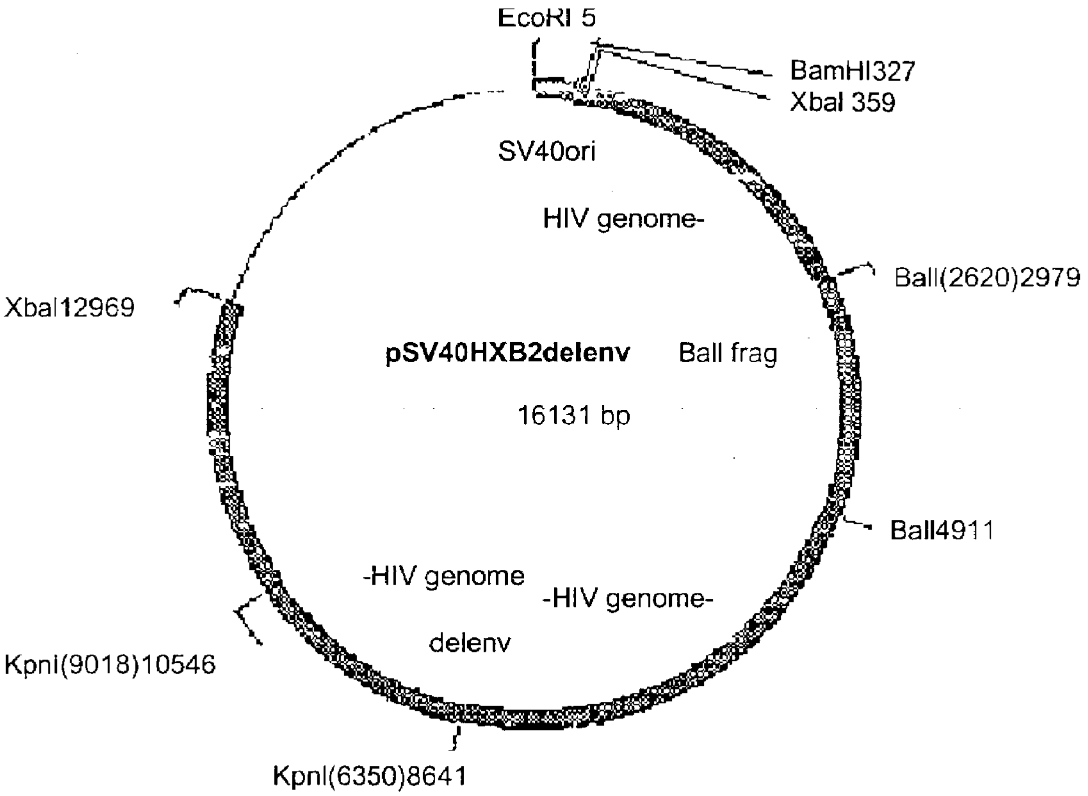
FIG. 7. Schematic representation of pSV40HXB2D env vector. The location of the HIV sequence is indicated in gray.

The pSV40HXB2D infectious clone was first digested using Bal I to remove a region of 1922 bp between nt 2620 and 4552, containing the KpnI I recognition site, then was religated. The resulting plasmid was called pSV40HXB2D Bal and is shown in FIG. 5. pSV40HXB2D Bal was treated with KpnI I to enable insertion of the pGEM ENV KpnI I fragment described above. This plasmid is shown in FIG. 6 and was called pSV40HXB2D Bal ENV. In the final step, the Bal region was re-inserted to complete construction of the infectious clone. The final vector was called pSV40HXB2D ENV and is shown in FIG. 7. A residual SmaI I recognition site remained at the site of the env deletion. This could be used for linearizing the vector before electroporation and subsequent homologous recombination. Alternatively, the patient derived env fragment could be inserted directly into the SmaI I site.

B) Design of a gp41 Deletion Plasmid

To create a plasmid without the gp41 part of the env gene, the env gene was amplified using PCR from the HXB2D GPRT vector and introduced into a pGEM vector by KpnI I digestion, creating pGEMENV, as described in part A. Using the primers 5'-ggg atc ctg cag ccc ggg ctt gga aag gcc-3' (SEQ ID NO:33) and 5'-ggg tgc tac tcc taa tgg ttc aat-3' (SEQ ID NO:34), containing SmaI I restriction sites, the gp41 coding region was effectively deleted from pGEMENV. The resulting construct was digested with SmaI I and re-ligated to create pGEM gp41. The remaining KpnI I insert was ligated into the pSV40HX2B infectious clone, as described for the env deletion plasmid, to create pSV40HX2B gp41. The gp41 deletion consists of 1053 base pairs from nucleotide 7717 to nucleotide 8770. The SmaI I site introduced by the primers was used for direct ligation of patient derived gp41 DNA into the infectious particle. Alternatively, the plasmid can be linearized by SmaI I digestion for homologous recombination.

The gp41 vector was also prepared by reintroducing the gp120 section of the env gene into the pGEM ENV vector described in part A. The gp120 fragment was amplified using pfu polymerase (Stratagene) and the primers: 5'-ata cat tat tgt gcc ccg gct gg-3' (SEQ ID NO:35) and 5'-ggg tgc tac tcc taa tgg ttc-3' (SEQ ID NO:36). This generated fragment was subsequently introduced into the pGEM ENV.

C) Design of a Full Env Deletion Plasmid

A different strategy was developed for the generation of full ENV deletion constructs, including the V1 and V2 loops, which were still present in the earlier constructs. The constructs were designed to yield a unique SmaI restriction recognition site into the vector. The pSV40HXB2D vector was used as a backbone to initiate the deletion by PCR. The construct described in option 1 constitutes a deletion in the tat gene. Since upon generation of chimeric viruses a chimeric tat gene could be generated (constituting partly from the plasmid backbone and partly derived from the patient), which could interfere with the infectivity of the chimeric particle, a second option was designed. In this second approach, the deletion was initiated upstream of the tat gene in order to get a tat which constitutes uniquely from a single biological source.

Option 1: Rev-Env

The wild-type Rev-Env deletion vector was constructed by deletion of the complete Env coding sequence (gp160) including Rev and most of Tat (leaving 10 AA N-terminal) (deletion of nucleotides 5860 to 8798 (in Nef start)->2938 bp deletion). The deletion was accomplished by PCR on pSV40HXB2D template with primers Env 3 and Env 5. After SmaI digestion the construct was religated.

Mutagenesis primers

| OLIGO NAME | SEQUENCE (5'-3') | SEQ ID NO |
|---|---|---|
| Env3 | GGGCTCTAGTCTAGGATCTACTGGCTCC | SEQ ID NO: 37 |
| Env5 | GGATCCTGCAGCCCGGGTGGCAAGTGGTCAAAAAGT | SEQ ID NO: 38 |

(SmaI tail, which is underlined, was used to facilitate cloning.)

Option 2: Tat-Rev-Env

The wild-type Tat-Rev-Env deletion vector was constructed by deletion of the complete Env coding sequence (gp160) including Tat and Rev (deletion of nucleotides 5572 (in Vif/Vpr start) to 8798 (in Nef start)->3226 bp deletion). The deletion was accomplished by PCR on pSV40HXB2D template with primers Env 4 and Env 5. After SmaI digestion the construct was religated.

Mutagenesis primers

| OLIGO NAME | SEQUENCE (5'-3') | SEQ ID NO |
|---|---|---|
| Env4 | GGGGCTTGTTCCATCTATCCTCTGTCAG | SEQ ID NO: 39 |
| Env5 | GGATCCTGCAGCCCGGGTGGCAAGTGGTCAAAAAGT | SEQ ID NO: 38 |

(SmaI tail, which is underlined, was used to facilitate cloning.)

Example 2

Reverse Transcription and PCR Amplification of Patient-derived HIV Sequences

The variability in the env gene is significantly higher than that of other HIV genes such as the pol genes. Therefore several series of primers that would be capable of efficiently reverse-transcribing and amplifying the env gene obtained from patient samples were designed. Oligonucleotides were developed which hybridized to the most conserved regions in the gene determined from alignment of HIV-1 complete genomes (HIV sequence database, see e.g. website hiv-web.lanl.gov). Over 150 different 5' and 3' primer combinations were originally tested for efficient amplification of env sequences from patient HIV isolates. These different combinations yielded up to 94% amplification in screening on 16 patient samples. Following optimization of the primer combinations, the four most efficient combinations were tested on 93 patient samples. For efficient amplification, two sets of primers were used in combination to yield amplification of 84% of the samples.

When only the gp41 region of the env gene was amplified, an additional set of 5' primers was tested. Three sets of primers were later tested on 90 patient samples of different subtypes. These three primer combinations supplied amplification in 81% of the samples. Generally, most of the clinical isolates analyzed belonged to the B subtype. The percentage of positive specific amplification of gp41 sequences from this subtype ranged from 74% to 76%.

HIV RNA was extracted from patient plasma using the QIAAMP® viral RNA extraction kit (Qiagen), according to the manufacturer's protocol. 10 µl of the extracted RNA was reverse transcribed for 30 minutes at 42° C. in a 20 µl volume with a commercial PCR buffer including 1.5 mM $MgCl_2$ at 1×strength, and an additional 3.5 mM $MgCl_2$, 0.75 µM 3' primer, 1 unit/µl of RNase inhibitor, 1 mM of each dNTP, and 0.33 units/µl of EXPAND® reverse transcriptase (Roche). Either the ENV3INN2 (SEQ ID NO:4) or ENV3OUT1 (SEQ ID NO:3) primers were used.

To amplify the reverse-transcribed fragment, a nested PCR procedure was performed, using sets of outer and inner primers. This method is described in Kellam, P. and Larder, B. A., (Antimicrobial Agents and Chemotherapy 38: 23-30 (1994)), which is incorporated herein by reference. After heat denaturation of the reverse transcription reaction at 99° C. for 5 minutes, 10 µl was added directly to the reaction mix for the outer PCR, described below. The 3' primer for the outer PCR is the same as that used for reverse transcription. When ENV3INN2 (SEQ ID NO:4) was used as the reverse transcription 3' primer, the env sequence was amplified either with ENV5OUTA (SEQ ID NO:11) the outer 5' primer and ENV5AA1001 (SEQ ID NO:8) and ENV3OUT1 (SEQ ID NO:3) as the inner primers, or with ENV5OUTC (SEQ ID NO:12) as the outer 5' primer and ENV5AA1002 (SEQ ID NO:9) and ENV3OUT1 (SEQ ID NO:3) as the inner primers. When ENV3OUT1 (SEQ ID NO:3) was used as the reverse transcription 3' primer, 5'EGENV1 (SEQ ID NO:10) was used as the outer 5' primer and ENV5OUT1 (SEQ ID NO:6) and ENV3AA1003 (SEQ ID NO:1) were used as the inner primers for env amplification. To amplify the gp41 part of env, ENV3INN2 (SEQ ID NO:4) was used for reverse transcription, while 5OUTgp41 (SEQ ID NO:19) was the outer 5' primer, and 5INNgp41A (SEQ ID NO:20) and ENV3OUT1 (SEQ ID NO:3) were the inner primers.

Different primers were used for the inner PCR for ligation experiments. These primers, cloning primers: 5'CPenv-P (SEQ ID NO:50) and 3'CP41-P (SEQ ID NO:49) for ligation in Env; 5'CP41-P (SEQ ID NO:48) and 3° CP41-P (SEQ ID NO:49) for ligation in gp41, enabled the insertion of the sample derived amplicon in the deletion construct without disrupting the reading frame. These sequences (Table 6) were phosphorylated at the 5 prime ends.

The outer PCR reaction was carried out in 100 µl with a commercial PCR buffer containing 1.5 mM $MgCl_2$ in the final reaction volume, an additional 1 mM $MgCl_2$, 0.2 mM each dNTP, 0.75 µM of the outer 5' primer, 10 µl of the reverse transcriptase reaction (including the 3' primer) and 0.05 units/µl of EXPAND® High Fidelity polymerase (Roche). After an initial denaturation at 95° C. for 3 minutes, thermal cycling for 30 cycles was performed, followed by a final extension for 10 minutes at 72° C. The thermal cycling procedure consisted of 1 minute at 90° C., 30 seconds at 60° C., and 2 minutes at 72° C.

Inner PCR reactions were performed with 5 µl of the outer PCR reaction in a 100 µl volume for 30 cycles using the same cycling procedure as for the outer PCR reactions. The reaction contained a commercial PCR buffer with 1.5 mM $MgCl_2$ at 1×concentration, an additional 1 mM $MgCl_2$, 0.2 mM of each dNTP, 0.15 µM of each primer, and 0.05 units/µl of EXPAND® High Fidelity polymerase.

To amplify the patient Rev-Env sequence, ENV3INN2 (SEQ ID NO:4) was used for reverse transcription, while 5LMENV3 (SEQ ID NO:42) or 5LMENV4 (SEQ ID NO: 43) was the 5' outer primer and 5LMENV1 (SEQ ID NO:40) and ENV3AA1003 (SEQ ID NO: 1) were the inner primers.

For amplification of the patient Tat-Rev-Env sequence, ENV3INN2 (SEQ ID NO: 4) was used for reverse transcription. For outer PCR, the reverse transcription primer can be used in combination with 5LMENV7 (SEQ ID NO: 46) or 5LMENV8 (SEQ ID NO: 47). For the inner PCR amplification, different primer combinations were possible: 5LMENV5 (SEQ ID NO:44) or 5LMENV6 (SEQ ID NO: 45) in combination with ENV3OUT1 (SEQ ID NO: 3), ENV3INN1 (SEQ ID NO: 2) or ENV3AA1003 (SEQ ID NO: 1).

PCR products were purified using the QIAQUICK® 96 PCR BioRobot kit (Qiagen), according to the manufacturer's protocol.

TABLE 7

Primer combinations for gp 160 PCR

| | RET | Outer PCR | | Inner PCR | |
|---|---|---|---|---|---|
| Primer set | 3'primer | 5'primer | 3'primer | 5'primer | 3'primer |
| Mix C 11 | ENV3INN2 | ENV5OUTA | (ENV3INN2) | ENV5AA1001 | ENV3OUT1 |
| Mix I 17 | ENV3INN2 | ENV5OUTC | (ENV3INN2) | ENV5AA1002 | ENV3OUT1 |
| Mix X 16 | ENV3OUT1 | 5'EGENV1 | (ENV3OUT1) | ENV5OUT1 | ENV3AA1003 |

TABLE 8

| Primer combination for gp41 PCR | | | | |
|---|---|---|---|---|
| RET | Outer PCR | | Inner PCR | |
| 3' primer | 5' primer | 3' primer | 5' primer | 3' primer |
| ENV3INN2 | 5'OUTgp41 | ENV3INN2 | 5'INNgp41A | 3ENV3OUT1 |

TABLE 9

RET Reaction mixture

| Compound | Final conc. |
|---|---|
| Milli-Q DEPC $H_2O$ | |
| PCR BI (15 mM $MgCl_2$) | 1.00 x |
| $MgCl_2$ | 3.50 mM |
| dNTP | 1.00 mM |
| 3' primer | 0.75 μM |
| RNase inhibitor | 1.00 U/μl |
| Expand RT | 0.33 U/μl |
| Volume reaction mix | 10 μl |
| Volume RNA | 10 μl |

TABLE 10

RET Program

| Step | Temp. | Time |
|---|---|---|
| Reverse transcription | 42° C. | 30 min |
| Denaturation/inactivation | 99° C. | 5 min |
| | 4° C. | hold |

TABLE 11

Outer PCR reaction mixture

| Compound | Final conc. |
|---|---|
| Milli-Q DEPC $H_2$ O | |
| PCR BI (15 mM $MgCl_2$) | 1.00 x |
| $MgCl_2$ | 1.00 mM |
| DNTP's | 0.20 mM |
| 5' primer | 0.75 μM |
| Expand HF | 0.05 U/μl |
| Volume reaction mix | 90 μl |
| Volume RET | 10 μl |

TABLE 12

Outer PCR program

| Step | Temp. | Time | |
|---|---|---|---|
| Initial denaturation | 95° C. | 3 min | |
| Denaturation | 90° C. | 1 min | 30 cycles |
| Annealing | 60° C. | 30 sec | 30 cycles |
| Elongation | 72° C. | 2 min | 30 cycles |
| Final extension | 72° C. | 10 min | |
| | 4° C. | hold | |

TABLE 13

Inner PCR reaction mixture

| Compound | Final conc. |
|---|---|
| Milli-Q DEPC $H_2O$ | |
| PCR BI (15 mM $MgCl_2$) | 1.00 x |
| $MgCl_2$ | 1.00 mM |
| DNTP's | 0.20 mM |
| 5' primer | 0.15 μM |
| 3' primer | 0.15 μM |
| Expand HF | 0.05 U/μl |
| Volume reaction mix | 95 μl |
| Volume outer | 5 μl |

TABLE 14

Inner PCR program

| Step | Temp. | Time | |
|---|---|---|---|
| Initial denaturation | 95° C. | 3 min | |
| Denaturation | 90° C. | 1 min | 30 cycles |
| Annealing | 60° C. | 30 sec | 30 cycles |
| Elongation | 72° C. | 2 min | 30 cycles |
| Final extension | 72° C. | 10 min | |
| | 4° C. | hold | |

Example 3 gp160 Recombination and Ligation

To produce recombinant virus, the linearized vector pSV40HXB2D ENV and the amplified env DNA, termed the env amplicon, were transfected by electroporation into MT4 cells or MT4 cells equipped with a LTR-reporter gene construct (MT4-rep). The normal MT4 cells may be used for the MTT-assay. The MT4 cells equipped with the LTR reporter gene, for example, have a reporter molecule, i.e. GFP under control of LTR.

By homologous recombination between overlapping parts of the vector and the env amplicon, the HIV genome was reconstituted with a patient derived env region. Production of recombinant virus was evaluated by scoring the cytopathogenic effect (CPE) that normally is induced by HIV infection of MT4 cells or by the induced LTR-driven reporter signal in MT4-rep cells. The viruses were harvested and titrated at maximum CPE.

A) Transfection of MT4 Cells with a Wild Type Env Amplicon

Recombination was first performed between a wild type env amplicon HXB2D and several clones of the pSV40HXB2D ENV vector in both MT4 and MT4-rep cells. Little difference was observed between the different pSV40HXB2D ENV clones. Full CPE was yielded at day 9 or 12. Results of these experiments are presented in Table 3.

B) Transfection of Cells with Patient Derived Env Amplicons

The HXB2D wild-type laboratory strain above is T-tropic and uses the CXCR4 co-receptor to infect cells. In contrast, most clinical strains are M-tropic and use the CCR5 co-receptor, which may not be expressed in MT4 or MT4-rep cells. Therefore, recombination experiments with patient env amplicons were performed with both the MT4 and MT4-rep cell lines and with the PM-1 cell line, which expresses both co-receptors. No CPE was observed after HXB2D or patient derived env amplicon transfection of PM-1 cells. However, in MT4 cells, Virco ID 133268, gave a strong reporter signal and a detectable but weak CPE. The titer of this sample was low. Transfection of the amplicon from Virco ID 133268 in PM-1 also gave a positive signal and a low but sufficient titer upon titration in PM-1. Table 3 provides a summary of these results.

C) Ligation of Env Coding Regions into an HIV Vector

Homologous recombination between the patient derived env sequences and the env gene in the pSV40HXB2D ENV vector can be avoided by cloning the patients' amplified env fragment into the SmaI I site of the vector. First, the vector was digested with SmaI I and dephosphorylated to prevent self-ligation. Patient derived env amplicons were then ligated into the vector after a similar SmaI I digestion. The resultant plasmid was used to transform competent *E. coli* cells. Colonies containing the correct env insert were identified and positive clones containing the patient fragment of Virco ID 133265 were obtained by this method. This clone was then transfected into PM-1 cells to produce recombinant virus particles.

TABLE 3

Overview env transfections

| Transfection | Cell type | Sample type | Number | Reporter activity | CPE | Titration |
|---|---|---|---|---|---|---|
| TRF00049R | MT4 | HXB2D | 13 | NA | − to ++ | Low titer |
| TRF00049R | MT4 | HXB2D | 2 | NA | +++ | OK |
| TRF00049R | MT4-rep | HXB2D | 6 | + to ++ | + to ++ | Low titer |
| TRF00049R | MT4-rep | HXB2D | 8 | ++ to +++ | ++ to +++ | OK |
| TRF00058R | MT4 | 4 patients | 17 | NA | − | ND |
| TRF00058R | MT4-rep | 4 patients | 17 | +/− | − | ND |
| TRF00063R | MT4 | HXB2D | 21 | NA | +/− | ND |
| TRF00066R | MT4-rep | HXB2D | 30 | ND | +/− | ND |
| TRF00069R | MT4-rep | HXB2D | 15 | ND | +++* | OK |
| TRF00074R | MT4-rep | HXB2D | 20 | ND | +++* | OK |
| TRF00076R | MT4-rep | HXB2D | 4 | ND | ++ to | OK |
| TRF00076R | MT4-rep | HXB2D | 11 | ND | − | ND |
| TRF01012R | MT4-rep | HXB2D | 1 | +/− | − | Low titer |
| TRE01012R | MT4-rep | HXB2D | 1 | +/− | − | OK |
| TRF01012R | MT4-rep | 10 patients | 10 | +/− | − | Low titer |
| TRF01012R | PM-1 | HXB2D | 2 | +/− | − | Low titer |
| TRF01012R | PM-1 | 9 patients | 9 | +/− | − | Low titer |
| TRF01012R | PM-1 | 133268 | 1 | +++* | + | OK |
| TRF01016R | PM-1 | HXB2D | 2 | +/− | − | Low titer |
| TRF01016R | PM-1 | 133268 | 1 | ++ | − | Low titer |
| TRF01016R | PM-1 | 15 patients | 15 | +/− | − | Low titer |

Legend:
NA: not applicable,
ND: not determined,
−: no infection, negative;
+/−: few cells infected;
+: ⅓ cell clusters is infected;
++: ⅔ cell clusters is infected;
+++almost all cell clusters are infected;
+++*almost every cell is infected
TRF00083R&D: TRF means transfection, R&D Research & Development.

Example 4 gp41 Recombination and Ligation

A) Transfection with Wild Type and Patient gp41 Amplicons

Transfection of the wild type HXB2D amplicon and pSV40HXB2D gp41 vector in MT4 cells reproducibly gave normal CPE and virus stocks with good titers. However, no CPE was observed in MT4 transfections with 15 patient samples. Transfection of MT4-rep cells with HXB2D resulted in a strong reporter signal, normal CPE and sufficient titer. The patient derived sample Virco ID 133268 gave a strong reporter signal and CPE at 13 days after electroporation in MT4-rep cells.

TABLE 4

| Overview gp4l transfections experiments | | | | | | |
|---|---|---|---|---|---|---|
| Transfection | Cell type | Sample type | Number | Reporter activity | CPE | Titration |
| TRF00083R | MT4 | HXB2D | 4 | NA | +++ | OK |
| TRF00083R | MT4 | 1 patient | 3 | NA | – | Low titer |
| TRF00086R | MT4 | HXB2D | 5 | NA | +++* | OK |
| TRF00086R | MT4 | 14 patients | 14 | NA | – | Low titer |
| TRF01023R | MT4-rep | HXB2D | 6 | +++* | +++* | OK |
| TRF01023R | MT4-rep | HXB2D | 1 | +/– | – | Low titer |
| TRF01023R | PM-1 | HXB2D | 1 | +/– | +/– | Low titer |
| TRF01023R | MT4-rep | 133268 | 3 | + to +++ | + to + | Low titer |
| TRF01023R | MT4-rep | 4 patients | 4 | +/– to + | – to +/– | Low titer |
| TRF01023R | PM-1 | 133268 | 1 | +/– | +/– | Low titer |
| TRF01023R | PM-1 | 4 patients | 4 | +/– | +/– | Low titer |

Legend:
NA: not applicable,
–: no infection, negative;
+/–: few cells infected;
+: ⅓ cell clusters is infected;
++: ⅔ cell clusters is infected;
+++almost all cell clusters are infected;
+++*almost every cell is infected.

B) Detection of Viral RNA and DNA in Transfected Cells

To confirm that recombinant viruses were formed in MT4 and MT4-rep cells transfected with wild type and patient derived gp41 amplicons, RNA and genomic DNA from these cells was extracted from frozen, electroporated cells. The RNA was DNase treated to remove traces of the originally added vector and amplicon. RNA was also extracted from the supernatant of electroporated cells and DNase treated. The samples were reverse transcribed (for the RNA) and PCR amplified to detect the (gag-protease-reverse transcriptase, GPRT) GPRT region and the entire env region including both gp120 and gp41 sections. The results are listed in table 5.

The fact that the env region could be amplified from the transfected cells proved that recombination between the gp41 amplicon and the pSV40HXB2D gp41 vector occurred after electroporation of MT4 or MT4-rep cells. Furthermore, this experiment demonstrated that viral RNA was present in the cells and in the supernatant of electroporated cells and that viral DNA was integrated into the cellular DNA of the electroporated cells.

C) Ligation of gp41 Amplicons into an HIV Vector

As an alternative to homologous recombination between patient amplicons and the wild-type env sequence in the pSV40HXB2D gp41 vector, the patients' gp41 fragment was digested with SmaI I and ligated into the SmaI I site of the pSV40HXB2D gp41 vector as described in Example 3 for the env sequence. Positive clones containing a gp41 insert in the correct orientation and a correct restriction pattern were obtained for the following Virco ID's: 133268, 133275, 133276, 142028 and 133266. Sequence analysis confirmed the correct ligation of the gp41 fragment in the vector for clones 133268 and 142028. Plasmid DNA for all 5 samples was then used to transfect electroporated MT4-rep cells. Sample 133268 gave a weak positive reporter signal and no CPE. CPE and reporter signals were not observed for the other samples. All samples were negative in titration.

TABLE 5

| Detection of HIV sequences in cells and cell supernatant | | | | | |
|---|---|---|---|---|---|
| Sample ID | Cells | GPRT PCR | Env PCR | GPRT PCR | Env PCR |
| | | RNA Cells | | DNA cells | |
| 132121 | MT4-rep | + | + | + | + |
| 132125 | MT4-rep | + | + | + | + |
| 132149 | MT4-rep | + | + | + | – |
| HXB2D | MT4-rep | + | + | + | + |
| pHXB2D | MT4-rep | + | + | + | + |
| 132121 | MT4 | + | – | + | – |
| 132125 | MT4 | + | – | + | – |
| 132149 | MT4 | + | + | + | + |
| HXB2D | MT4 | + | + | + | + |
| pHXB2D | MT4 | + | + | + | + |
| | | RNA supernatant | | | |
| 132121 | MT4-rep | + | + | | |
| 132125 | MT4-rep | + | + | | |
| 132149 | MT4-rep | + | + | | |
| HXB2D | MT4-rep | + | + | | |
| pHXB2D | MT4-rep | + | – | | |
| 132121 | MT4 | +/– | + | | |
| 132125 | MT4 | + | + | | |
| 132149 | MT4 | + | + | | |
| HXB2D | MT4 | + | – | | |
| pHXB2D | MT4 | + | + | | |

Legend: pHXB2D transfection (full circle with intact HXB2D) as positive control

TABLE 6

List of gp41 cloning primers
CLONING PRIMERS

| OLIGO NAME | SEQ ID NO. | MW | MW | Tm | SEQUENCE (5'-3') |
|---|---|---|---|---|---|
| 5'CP41-P | SEQ ID NO:48 | 24 | 7588.9 | 68.4 | P-ACCAAGGCAAAGAGAAGAGTGGTG |
| 3'CP41-P | SEQ ID NO:49 | 26 | 8081.0 | 61.1 | P-TGTCTTATTCTTCTAGGTATGTGGMG |
| 5'CPenv-P | SEQ ID NO:50 | 22 | 6781.2 | 68.4 | P-ATACATTATTGTGCCCCGGCTG |

Example 5

Full Env (Tat)-Rev-Env Recombination

To produce recombinant virus, the linearized wild type deletion vectors pSV40HXB2D Rev-Env and pSV40HXBD Tat-Rev-Env were co-transfected with the corresponding env sequences (Rev-Env and Tat-Rev-Env respectively) into MT4-reporter cells. Recombination was performed with wild type HXB2D sequences and yielded for both deletion constructs in full CPE at day 8 post transfection.

Example 6

Genotyping of Patient Derived Env Amplicons

A) Obtaining and Amplifying Patient Derived Env Sequences

See Example 2.

B) Sequencing of Env Coding Region

The sequencing was started by first distributing 4 µl of the primer stocks (4.0 µM) over a 96 well plate. In a second step, master mixes were made consisting of 14 µl deionized water, 17.5 µl dilution buffer, 7 µl sample (PCR fragment) and 14 µl Big Dye™ Terminator Mix (Perkin Elmer). A fraction (7.5 µl ) of each master mix, containing a specific PCR fragment, was transferred to a specific place into the 96 well plate so that each sample fraction was mixed with a different PCR primer set. Samples were pipetted across the rows. The samples were placed in a thermal cycler and sequencing cycles started, which consisted of 25 repetitive cycles of 10 sec at 96° C., 5 sec at 50° C. and 4 min at 60° C., respectively. Finally, sequence reactions were held at 4° C. or frozen until further analysis. The sequencing reactions were precipitated using a standard ethanol precipitation procedure, resuspended in 2 µl formamide and heated for 2 minutes at 92° C. in the thermal cycler. Samples were cooled on ice until ready to load. 1 µl of each reaction was loaded on a 4.25% vertical acrylamide gel in a 377 sequencer system and gel was run until separation of the fragments was complete.

C) Sequence Analysis of Env Coding Region

Sample sequences were imported as a specific project into the sequence manager of Sequencher (Genecodes, Applied Biosystems) and compared to the wild type HXB2D env reference sequence. Sequences were assembled automatically and set at 85% minimum match. Secondary peaks were searched and the minimum was set at 60%. Any sequence that extended beyond the 5' end or the 3' end of the reference was deleted. When a region of overlap between sequences from the same strand was reached, the poorest quality of sequence was deleted leaving an overlap of 5-10 bases. Ambiguous base calls were considered poor matches to exact base calls. The sequence assembly was saved within a contig that could be edited.

Obtained sequences were edited so that base calls could be interpreted easily. Ambiguous sequences were retrieved and checked for possible errors or points of heterogeneity. When the point of ambiguity appeared correct (both strands of sequence agreed but were different from the reference sequence) it was interpreted to be a variant. The reference sequence was used as an aid for building a contig and a guide to overall size and for trimming, but was not used for deciding base calls. A change was only made when both strands agreed. All gaps were deleted or filled, unless they occurred in contiguous groups of multiples of three (i.e., insertion or deletion of complete codons) based on data form both sequence strands. Once the editing was complete, the new contig sequence was saved as a consensus sequence and used for further analysis.

Detailed sequence editing was performed following certain rules: A) Applied Biosystems, Inc. primer blocks were trimmed at 5' ends where 1 consecutive base remained off the scale, the sequence was trimmed not more than 25% until the first 25 bases contained less than 1 ambiguity, at least the first 10 bases from the 5' end were removed, and B) 3' ends were trimmed starting 300 bases after the 5' trim, the first 25 bases containing more than 2 ambiguities were removed, the 3' end was trimmed until the last 25 bases contained less than 1 ambiguity. The maximum length of the obtained sequence fragment after trimming was 550 bases.

Sequences that failed to align were removed from the assembly and replaced by data retrieved from new sequence analyses. When further failures occurred, PCR reactions were repeated. Chromatograms were visualized using an IBM software system.

The nucleotide sequence of gp41 was determined as described in section B of this example for Virco ID's 133268, 133275, 133276 and 142028. The gp41 primers of SEQ ID NO:24-SEQ ID NO:31 were used. The alignment of the corresponding amino acid sequence with the HXB2D wild type amino acid sequence was obtained as described in this section and is presented in FIG. 8.

The invention claimed is:

1. A method for determining the phenotypic susceptibility of at least one human immunodeficiency virus to at least one drug, comprising:

i) obtaining at least one sample comprising human immunodeficiency virus (HIV) RNA, wherein the sample comprises at least one envelope (env) gene or a portion thereof, wherein the portion thereof includes at least gp160, gp120 or gp41;

ii) reverse-transcribing and amplifying the HIV RNA, with primers specific for env region of the HIV genome, to obtain at least one amplicon comprising the at least one env gene or a portion thereof, wherein the portion thereof includes at least gp160, gp120 or gp41 wherein at least one primer is selected from SEQ ID NO: 1, 3, 4, 6, 10, 19 and 20;

iii) using nucleic acid amplification to generate at least one plasmid containing a wild-type HIV sequence with a deletion in the env region comprising at least 500 bp of the HIV env gene;

iv) homologously recombining or ligating the at least one amplicon with the at least one plasmid comprising the wild-type HIV sequence with a deletion in the env gene or a portion thereof, wherein the portion thereof includes at least gp160, gp120 or gp41, to prepare at least one recombinant virus; and v) monitoring the at least one recombinant virus in the presence of the at least one drug to determine the phenotypic susceptibility, wherein the phenotypic susceptibility of at least one human immunodeficiency virus to at least one drug is determined by the replicative capacity of the at least one recombinant virus in the presence of the at least one drug.

2. The method according to claim 1 for designing a treatment regimen for an HIV infected patient, wherein the treatment regimen is selected based on the replicative capacity of the at least one recombinant virus in the presence of the at least one drug.

3. A method for determining the susceptibility of at least one human immunodeficiency virus to at least one drug, comprising:

i) obtaining at least one sample comprising HIV RNA, wherein the sample comprises at least one env gene or a portion thereof, wherein the portion thereof includes at least gp160, gp120 or gp41;

ii) reverse-transcribing and amplifying the HIV RNA, with primers specific for the env region of the HIV genome, to obtain at least one amplicon comprising the env gene or a portion thereof, wherein the portion thereof includes at least gp160, gp120 or gp41 wherein at least one primer is selected from SEQ ID NO: 1, 3, 4, 6, 10, 19 and 20;

iii) determining the nucleotide sequence of the at least one amplicon or a portion thereof iv) comparing the nucleotide sequence of the at least one amplicon or portion thereof to the sequence of known sequences; and v) correlating sequence differences between the at least one amplicon or portion thereof and the sequence of known sequences wherein the sequence differences indicate a change in drug efficacy; thereby determining the susceptibility of at least one human immunodeficiency virus to at least one drug.

4. A method according to claim 2 suitable for high throughput screening.

5. A method according to claim 3 suitable for high throughput screening.

* * * * *

UNITED STATES PATENT AND TRADEMARK OFFICE

CERTIFICATE OF CORRECTION

PATENT NO. : 7,306,901 B2
APPLICATION NO. : 10/214670
DATED : December 11, 2007
INVENTOR(S) : Sharon Kemp et al.

It is certified that error appears in the above-identified patent and that said Letters Patent is hereby corrected as shown below:

Title Page,
Item (30) Foreign Application Priority Data:
After "01203011" insert -- .0 --.

Title Page,
Insert missing Related U.S. Application Data:

-- Related U.S. Application Data
(60) Provisional application No. 60/310,497, filed on August 8, 2001. --.

Columns 5-6,
TABLE 1-continued, Mutagenesis Primers section, line 5, delete "GGATCCTGCAGCCCGGGTGGCAAGTGGTCAAAAACT" and insert -- GGATCCTGCAGCCCGGGTGGCAAGTGGTCAAAAAGT --.

Columns 25-26,
TABLE 4, column "CPE", line 8, delete "+ to +" and insert -- - to + --.

Column 54,
Line 32, after "thereof" insert -- ; --.

Signed and Sealed this

Ninth Day of December, 2008

JON W. DUDAS
*Director of the United States Patent and Trademark Office*

SEQUENCE LISTING

<160> NUMBER OF SEQ ID NOS: 62

<210> SEQ ID NO 1
<211> LENGTH: 26
<212> TYPE: DNA
<213> ORGANISM: Human immunodeficiency virus

<400> SEQUENCE: 1
attctttccc ttacagcagg ccatcc 26

<210> SEQ ID NO 2
<211> LENGTH: 22
<212> TYPE: DNA
<213> ORGANISM: Human immunodeficiency virus

<400> SEQUENCE: 2
gctcctactc cttctgctgc tg 22

<210> SEQ ID NO 3
<211> LENGTH: 26
<212> TYPE: DNA
<213> ORGANISM: Human immunodeficiency virus

<400> SEQUENCE: 3
cttaaaggta cctgaggtct gactgg 26

<210> SEQ ID NO 4
<211> LENGTH: 24
<212> TYPE: DNA
<213> ORGANISM: Human immunodeficiency virus

<400> SEQUENCE: 4
ggtgtgtagt tctgccaatc aggg 24

<210> SEQ ID NO 5
<211> LENGTH: 28
<212> TYPE: DNA
<213> ORGANISM: Human immunodeficiency virus

<400> SEQUENCE: 5
caactggtac tagcttgaag caccatcc 28

<210> SEQ ID NO 6
<211> LENGTH: 27
<212> TYPE: DNA
<213> ORGANISM: Human immunodeficiency virus

<400> SEQUENCE: 6
cctaaagcca tgtgtaaagt taacccc 27

<210> SEQ ID NO 7
<211> LENGTH: 24
<212> TYPE: DNA
<213> ORGANISM: Human immunodeficiency virus

<400> SEQUENCE: 7
ccattacaca ggcttgtcca aagg 24

<210> SEQ ID NO 8
<211> LENGTH: 26
<212> TYPE: DNA
<213> ORGANISM: Human immunodeficiency virus -continued

<400> SEQUENCE: 8
gcatgaggat ataatcagtt tatggg 26

<210> SEQ ID NO 9
<211> LENGTH: 26
<212> TYPE: DNA
<213> ORGANISM: Human immunodeficiency virus

<400> SEQUENCE: 9
tgtaatacct cagtcattac acaggc 26

<210> SEQ ID NO 10
<211> LENGTH: 27
<212> TYPE: DNA
<213> ORGANISM: Human immunodeficiency virus

<400> SEQUENCE: 10
gggatcaaag cctaaagcca tgtgtaa 27

<210> SEQ ID NO 11
<211> LENGTH: 26
<212> TYPE: DNA
<213> ORGANISM: Human immunodeficiency virus

<400> SEQUENCE: 11
tgggtacctg tgtggaaaga agcaac 26

<210> SEQ ID NO 12
<211> LENGTH: 25
<212> TYPE: DNA
<213> ORGANISM: Human immunodeficiency virus

<400> SEQUENCE: 12
gtttgggcca cacatgcctg tgtac 25

<210> SEQ ID NO 13
<211> LENGTH: 25
<212> TYPE: DNA
<213> ORGANISM: Human immunodeficiency virus

<400> SEQUENCE: 13
cacacatgcc tgtgtaccca cagac 25

<210> SEQ ID NO 14
<211> LENGTH: 27
<212> TYPE: DNA
<213> ORGANISM: Human immunodeficiency virus

<400> SEQUENCE: 14
gtgtggaaag aagcaaccac cactcta 27

<210> SEQ ID NO 15
<211> LENGTH: 26
<212> TYPE: DNA
<213> ORGANISM: Human immunodeficiency virus

<400> SEQUENCE: 15
gtgggtcaca gtctattatg gggtac 26

<210> SEQ ID NO 16
<211> LENGTH: 26
<212> TYPE: DNA

-continued

<213> ORGANISM: Human immunodeficiency virus

<400> SEQUENCE: 16
ccacagaccc caacccacaa gaagta 26

<210> SEQ ID NO 17
<211> LENGTH: 27
<212> TYPE: DNA
<213> ORGANISM: Human immunodeficiency virus

<400> SEQUENCE: 17
cagaggtaca taatgtttgg gccacac 27

<210> SEQ ID NO 18
<211> LENGTH: 23
<212> TYPE: DNA
<213> ORGANISM: Human immunodeficiency virus

<400> SEQUENCE: 18
cctcaggagg ggaccyagaa att 23

<210> SEQ ID NO 19
<211> LENGTH: 26
<212> TYPE: DNA
<213> ORGANISM: Human immunodeficiency virus

<400> SEQUENCE: 19
ggamaagcaa tgtatgcccc tcccat 26

<210> SEQ ID NO 20
<211> LENGTH: 24
<212> TYPE: DNA
<213> ORGANISM: Human immunodeficiency virus

<400> SEQUENCE: 20
cttcagacct ggaggaggag atat 24

<210> SEQ ID NO 21
<211> LENGTH: 25
<212> TYPE: DNA
<213> ORGANISM: Human immunodeficiency virus

<400> SEQUENCE: 21
ggagatatga gggacaattg gagaa 25

<210> SEQ ID NO 22
<211> LENGTH: 25
<212> TYPE: DNA
<213> ORGANISM: Human immunodeficiency virus

<400> SEQUENCE: 22
cctggaggag gagatatgag ggaca 25

<210> SEQ ID NO 23
<211> LENGTH: 21
<212> TYPE: DNA
<213> ORGANISM: Human immunodeficiency virus

<400> SEQUENCE: 23
ccattaggag tagcacccac c 21

<210> SEQ ID NO 24
<211> LENGTH: 18

-continued

<212> TYPE: DNA
<213> ORGANISM: Human immunodeficiency virus

<400> SEQUENCE: 24
gggacaattg gagaagtg 18

<210> SEQ ID NO 25
<211> LENGTH: 19
<212> TYPE: DNA
<213> ORGANISM: Human immunodeficiency virus

<400> SEQUENCE: 25
gaatcgcaga accagcagg 19

<210> SEQ ID NO 26
<211> LENGTH: 20
<212> TYPE: DNA
<213> ORGANISM: Human immunodeficiency virus

<400> SEQUENCE: 26
ccaattccac agacttgccc 20

<210> SEQ ID NO 27
<211> LENGTH: 21
<212> TYPE: DNA
<213> ORGANISM: Human immunodeficiency virus

<400> SEQUENCE: 27
gctccaggca agagtcctgg c 21

<210> SEQ ID NO 28
<211> LENGTH: 22
<212> TYPE: DNA
<213> ORGANISM: Human immunodeficiency virus

<400> SEQUENCE: 28
gagttaggca gggatactca cc 22

<210> SEQ ID NO 29
<211> LENGTH: 18
<212> TYPE: DNA
<213> ORGANISM: Human immunodeficiency virus

<400> SEQUENCE: 29
ctctccacct tcttcttc 18

<210> SEQ ID NO 30
<211> LENGTH: 26
<212> TYPE: DNA
<213> ORGANISM: Human immunodeficiency virus

<400> SEQUENCE: 30
gcagatgagt tttccagagc agcccc 26

<210> SEQ ID NO 31
<211> LENGTH: 20
<212> TYPE: DNA
<213> ORGANISM: Human immunodeficiency virus

<400> SEQUENCE: 31
ctttttgacc acttgccacc 20

<210> SEQ ID NO 32

-continued

```
<211> LENGTH: 27
<212> TYPE: DNA
<213> ORGANISM: Human immunodeficiency virus

<400> SEQUENCE: 32

gggaattggc tcaaaggata cctttgg                                          27


<210> SEQ ID NO 33
<211> LENGTH: 30
<212> TYPE: DNA
<213> ORGANISM: Human immunodeficiency virus

<400> SEQUENCE: 33

gggatcctgc agcccgggct tggaaaggcc                                       30


<210> SEQ ID NO 34
<211> LENGTH: 24
<212> TYPE: DNA
<213> ORGANISM: Human immunodeficiency virus

<400> SEQUENCE: 34

gggtgctact cctaatggtt caat                                             24


<210> SEQ ID NO 35
<211> LENGTH: 23
<212> TYPE: DNA
<213> ORGANISM: Human immunodeficiency virus

<400> SEQUENCE: 35

atacattatt gtgccccggc tgg                                              23


<210> SEQ ID NO 36
<211> LENGTH: 21
<212> TYPE: DNA
<213> ORGANISM: Human immunodeficiency virus

<400> SEQUENCE: 36

gggtgctact cctaatggtt c                                                21


<210> SEQ ID NO 37
<211> LENGTH: 28
<212> TYPE: DNA
<213> ORGANISM: Human immunodeficiency virus

<400> SEQUENCE: 37

gggctctagt ctaggatcta ctggctcc                                         28


<210> SEQ ID NO 38
<211> LENGTH: 36
<212> TYPE: DNA
<213> ORGANISM: Human immunodeficiency virus

<400> SEQUENCE: 38

ggatcctgca gcccgggtgg caagtggtca aaaagt                                36


<210> SEQ ID NO 39
<211> LENGTH: 28
<212> TYPE: DNA
<213> ORGANISM: Human immunodeficiency virus

<400> SEQUENCE: 39

ggggcttgtt ccatctatcc tctgtcag                                         28
```

-continued

<210> SEQ ID NO 40
<211> LENGTH: 24
<212> TYPE: DNA
<213> ORGANISM: Human immunodeficiency virus

<400> SEQUENCE: 40
ttgggtgtca acatagcaga atag 24

<210> SEQ ID NO 41
<211> LENGTH: 24
<212> TYPE: DNA
<213> ORGANISM: Human immunodeficiency virus

<400> SEQUENCE: 41
ctgtttattc attttcagaa ttgg 24

<210> SEQ ID NO 42
<211> LENGTH: 25
<212> TYPE: DNA
<213> ORGANISM: Human immunodeficiency virus

<400> SEQUENCE: 42
ctatgaaact tatggggata cttgg 25

<210> SEQ ID NO 43
<211> LENGTH: 23
<212> TYPE: DNA
<213> ORGANISM: Human immunodeficiency virus

<400> SEQUENCE: 43
gctccatggc ttaggacaac ata 23

<210> SEQ ID NO 44
<211> LENGTH: 24
<212> TYPE: DNA
<213> ORGANISM: Human immunodeficiency virus

<400> SEQUENCE: 44
agataaagcc acctttgcct agtg 24

<210> SEQ ID NO 45
<211> LENGTH: 24
<212> TYPE: DNA
<213> ORGANISM: Human immunodeficiency virus

<400> SEQUENCE: 45
gacataacaa ggtaggatct ctac 24

<210> SEQ ID NO 46
<211> LENGTH: 24
<212> TYPE: DNA
<213> ORGANISM: Human immunodeficiency virus

<400> SEQUENCE: 46
atcaagcagg acataacaag gtag 24

<210> SEQ ID NO 47
<211> LENGTH: 21
<212> TYPE: DNA
<213> ORGANISM: Human immunodeficiency virus

<400> SEQUENCE: 47
gcagaccaac taattcatct g 21

-continued

<210> SEQ ID NO 48
<211> LENGTH: 24
<212> TYPE: DNA
<213> ORGANISM: Human immunodeficiency virus

<400> SEQUENCE: 48
accaaggcaa agagaagagt ggtg 24

<210> SEQ ID NO 49
<211> LENGTH: 26
<212> TYPE: DNA
<213> ORGANISM: Human immunodeficiency virus

<400> SEQUENCE: 49
tgtcttattc ttctaggtat gtggmg 26

<210> SEQ ID NO 50
<211> LENGTH: 22
<212> TYPE: DNA
<213> ORGANISM: Human immunodeficiency virus

<400> SEQUENCE: 50
atacattatt gtgccccggc tg 22

<210> SEQ ID NO 51
<211> LENGTH: 18
<212> TYPE: DNA
<213> ORGANISM: Human immunodeficiency virus

<400> SEQUENCE: 51
atgctccttg ggatgttg 18

<210> SEQ ID NO 52
<211> LENGTH: 18
<212> TYPE: DNA
<213> ORGANISM: Human immunodeficiency virus

<400> SEQUENCE: 52
aaccccactc tgtgttag 18

<210> SEQ ID NO 53
<211> LENGTH: 20
<212> TYPE: DNA
<213> ORGANISM: Human immunodeficiency virus

<400> SEQUENCE: 53
cccatacatt attgtgcccc 20

<210> SEQ ID NO 54
<211> LENGTH: 18
<212> TYPE: DNA
<213> ORGANISM: Human immunodeficiency virus

<400> SEQUENCE: 54
gttttaattg tggagggg 18

<210> SEQ ID NO 55
<211> LENGTH: 18
<212> TYPE: DNA
<213> ORGANISM: Human immunodeficiency virus

<400> SEQUENCE: 55
gtgcttcctg ctgctccc 18

-continued

<210> SEQ ID NO 56
<211> LENGTH: 18
<212> TYPE: DNA
<213> ORGANISM: Human immunodeficiency virus

<400> SEQUENCE: 56
ggcatacatt gcttttcc 18

<210> SEQ ID NO 57
<211> LENGTH: 20
<212> TYPE: DNA
<213> ORGANISM: Human immunodeficiency virus

<400> SEQUENCE: 57
ggggcacaat aatgtatggg 20

<210> SEQ ID NO 58
<211> LENGTH: 359
<212> TYPE: PRT
<213> ORGANISM: Human immunodeficiency virus

<400> SEQUENCE: 58

Lys Ile Glu Pro Leu Gly Val Ala Pro Thr Lys Ala Lys Arg Arg Val
1 5 10 15

Val Gln Arg Glu Lys Arg Ala Val Gly Ile Gly Ala Leu Phe Leu Gly
20 25 30

Phe Leu Gly Ala Ala Gly Ser Thr Met Gly Ala Ala Ser Met Thr Leu
35 40 45

Thr Val Gln Ala Arg Gln Leu Leu Ser Gly Ile Val Gln Gln Gln Asn
50 55 60

Asn Leu Leu Arg Ala Ile Glu Ala Gln Gln His Leu Leu Gln Leu Thr
65 70 75 80

Val Trp Gly Ile Lys Gln Leu Gln Ala Arg Ile Leu Ala Val Glu Arg
85 90 95

Tyr Leu Lys Asp Gln Gln Leu Leu Gly Ile Trp Gly Cys Ser Gly Lys
100 105 110

Leu Ile Cys Thr Thr Ala Val Pro Trp Asn Ala Ser Trp Ser Asn Lys
115 120 125

Ser Leu Glu Gln Ile Trp Asn His Thr Thr Trp Met Glu Trp Asp Arg
130 135 140

Glu Ile Asn Asn Tyr Thr Ser Leu Ile His Ser Leu Ile Glu Glu Ser
145 150 155 160

Gln Asn Gln Gln Glu Lys Asn Glu Gln Glu Leu Leu Glu Leu Asp Lys
165 170 175

Trp Ala Ser Leu Trp Asn Trp Phe Asn Ile Thr Asn Trp Leu Trp Tyr
180 185 190

Ile Lys Leu Phe Ile Met Ile Val Gly Gly Leu Val Gly Leu Arg Ile
195 200 205

Val Phe Ala Val Leu Ser Ile Val Asn Arg Val Arg Gln Gly Tyr Ser
210 215 220

Pro Leu Ser Phe Gln Thr His Leu Pro Ile Pro Arg Gly Pro Asp Arg
225 230 235 240

Pro Glu Gly Ile Glu Glu Glu Gly Gly Glu Arg Asp Arg Asp Arg Ser
245 250 255

Ile Arg Leu Val Asn Gly Ser Leu Ala Leu Ile Trp Asp Asp Leu Arg
260 265 270

-continued

```
Ser Leu Cys Leu Phe Ser Tyr His Arg Leu Arg Asp Leu Leu Leu Ile
        275                 280                 285

Val Thr Arg Ile Val Glu Leu Leu Gly Arg Arg Gly Trp Glu Ala Leu
    290                 295                 300

Lys Tyr Trp Trp Asn Leu Leu Gln Tyr Trp Ser Gln Glu Leu Lys Asn
305                 310                 315                 320

Ser Ala Val Ser Leu Leu Asn Ala Thr Ala Ile Ala Val Ala Glu Gly
                325                 330                 335

Thr Asp Arg Val Ile Glu Val Val Gln Gly Ala Cys Arg Ala Ile Arg
            340                 345                 350

His Ile Pro Arg Arg Ile Arg
        355


<210> SEQ ID NO 59
<211> LENGTH: 360
<212> TYPE: PRT
<213> ORGANISM: Human immunodeficiency virus

<400> SEQUENCE: 59

Arg Ile Glu Pro Leu Gly Val Ala Pro Thr Glu Ala Lys Arg Arg Val
  1               5                  10                  15

Val Gln Arg Glu Lys Arg Ala Val Val Gly Ile Gly Ala Leu Phe Leu
             20                  25                  30

Gly Phe Leu Gly Thr Ala Gly Ser Thr Met Gly Ala Ala Ser Leu Thr
         35                  40                  45

Leu Thr Val Gln Ala Arg Gln Leu Leu Ser Gly Ile Val Gln Gln Gln
     50                  55                  60

Asn Asn Leu Leu Arg Ala Ile Glu Ala Gln Gln His Leu Leu Gln Leu
 65                  70                  75                  80

Thr Val Trp Gly Ile Lys Gln Leu Gln Ala Arg Val Leu Ala Val Glu
                 85                  90                  95

Arg Tyr Leu Arg Asp Gln Gln Leu Leu Gly Ile Trp Gly Cys Ser Gly
            100                 105                 110

Lys Leu Ile Cys Thr Thr Thr Val Pro Trp Asn Thr Ser Trp Ser Asn
        115                 120                 125

Lys Thr Leu Asn Glu Ile Trp Asp Asn Met Thr Trp Met Glu Trp Asp
    130                 135                 140

Arg Gln Ile Ser Asn Tyr Thr Glu Val Ile Tyr Ser Leu Leu Glu Glu
145                 150                 155                 160

Ser Gln Asn Gln Gln Glu Lys Asn Glu Gln Glu Leu Leu Ala Leu Asp
                165                 170                 175

Lys Trp Ala Ser Leu Trp Asn Trp Phe Asp Ile Thr Lys Trp Leu Trp
            180                 185                 190

Tyr Ile Lys Ile Phe Ile Met Ile Val Gly Gly Leu Val Gly Leu Arg
        195                 200                 205

Ile Val Phe Thr Val Leu Ser Ile Val Asn Arg Val Arg Gln Gly Tyr
    210                 215                 220

Ser Pro Leu Ser Phe Gln Thr His Leu Pro Thr Pro Arg Gly Pro Asp
225                 230                 235                 240

Arg Pro Glu Gly Ile Glu Gly Glu Gly Gly Asp Lys Asp Arg Asp Arg
                245                 250                 255

Ser Ser Gly Leu Val Thr Gly Phe Leu Ala Leu Ile Trp Val Asp Leu
            260                 265                 270

Arg Asn Leu Phe Leu Phe Ser Tyr His Arg Leu Arg Asp Leu Leu Leu
```

-continued

```
        275                 280                 285

Ile Val Thr Arg Ile Val Glu Leu Leu Gly Arg Gly Gly Trp Glu Thr
    290                 295                 300

Leu Lys Tyr Trp Trp Asn Leu Leu Gln Tyr Trp Ser Gln Glu Leu Lys
305                 310                 315                 320

Asn Ser Ala Ile Ser Leu Leu Asn Ala Thr Ala Ile Ala Val Ala Glu
                325                 330                 335

Gly Thr Asp Arg Val Ile Glu Ile Leu Gln Arg Ile Phe Arg Ala Val
            340                 345                 350

Ile His Val Pro Arg Arg Ile Arg
        355                 360


<210> SEQ ID NO 60
<211> LENGTH: 360
<212> TYPE: PRT
<213> ORGANISM: Human immunodeficiency virus

<400> SEQUENCE: 60

Gln Ile Glu Pro Leu Gly Val Ala Pro Thr Lys Ala Lys Arg Arg Val
  1               5                  10                  15

Val Gln Arg Glu Lys Arg Ala Val Gly Ala Ile Gly Ala Met Phe Leu
             20                  25                  30

Gly Phe Leu Gly Ala Ala Gly Ser Thr Met Gly Ala Ala Ser Met Ala
         35                  40                  45

Leu Thr Val Gln Ala Arg Gln Leu Leu Ser Gly Ile Val Gln Gln Gln
     50                  55                  60

Asn Asn Leu Leu Arg Ala Ile Glu Ala Gln Gln His Leu Leu Gln Leu
 65                  70                  75                  80

Thr Val Trp Gly Ile Lys Gln Leu Gln Ala Arg Val Leu Ala Val Glu
                 85                  90                  95

Arg Tyr Leu Lys Asp Gln Gln Leu Leu Gly Ile Trp Gly Cys Ser Gly
            100                 105                 110

Lys Leu Ile Cys Thr Thr Ala Val Pro Trp Asn Thr Ser Trp Ser Asn
        115                 120                 125

Lys Ser Leu Ser Gln Ile Trp Asp Asn Met Thr Trp Met Glu Trp Glu
    130                 135                 140

Arg Glu Ile Asp Asn Tyr Thr Gly Leu Ile Tyr Asn Leu Ile Glu Glu
145                 150                 155                 160

Ser Gln Asn Gln Gln Glu Lys Asn Glu Lys Asp Leu Leu Glu Leu Asn
                165                 170                 175

Ser Trp Ala Ser Leu Trp Asn Trp Phe Asp Ile Ser Asn Trp Leu Trp
            180                 185                 190

Tyr Ile Lys Ile Phe Ile Met Ile Val Gly Gly Leu Ile Gly Leu Arg
        195                 200                 205

Ile Val Phe Ala Val Leu Ser Ile Val Asn Arg Val Arg Pro Glu Gly
    210                 215                 220

Ile Glu Glu Glu Gly Gly Glu Arg Asp Arg Asp Arg Ser Val Arg Leu
225                 230                 235                 240

Arg Gln Gly Tyr Ser Pro Leu Ser Phe Gln Thr Leu Leu Pro Ala Ser
                245                 250                 255

Arg Gly Pro Asp Val Asn Gly Phe Leu Ala Leu Val Trp Asp Asp Leu
            260                 265                 270

Arg Ser Leu Cys Leu Phe Ser Tyr His Arg Leu Arg Asp Leu Leu Leu
        275                 280                 285
```

-continued

```
Ile Val Ala Arg Thr Val Glu Leu Leu Gly Arg Arg Gly Trp Glu Ile
    290                 295                 300

Leu Lys Tyr Trp Gly Asn Leu Leu Gln Tyr Trp Ser Gln Glu Ile Arg
305                 310                 315                 320

Asn Ser Ala Val Ser Leu Leu Asp Thr Thr Ala Ile Ala Val Ala Glu
                325                 330                 335

Gly Thr Asp Arg Ile Ile Glu Ile Ala Gln Arg Val Phe Arg Ala Phe
            340                 345                 350

Leu His Ile Pro Arg Arg Ile Arg
        355                 360


<210> SEQ ID NO 61
<211> LENGTH: 360
<212> TYPE: PRT
<213> ORGANISM: Human immunodeficiency virus

<400> SEQUENCE: 61

Arg Ile Glu Pro Leu Gly Ile Ala Pro Asn Lys Ala Lys Arg Arg Val
  1               5                  10                  15

Val Gln Arg Glu Lys Arg Ala Ile Gly Ala Leu Gly Ala Met Phe Leu
            20                  25                  30

Gly Phe Leu Gly Thr Ala Gly Ser Thr Met Gly Ala Ala Ser Leu Thr
        35                  40                  45

Leu Thr Val Gln Ala Arg Gln Leu Leu Ser Gly Ile Val Gln Gln Gln
    50                  55                  60

Asn Asn Leu Leu Arg Ala Ile Glu Ala Gln Gln His Leu Leu Gln Leu
65                  70                  75                  80

Thr Val Trp Gly Ile Lys Gln Leu Gln Ala Arg Val Leu Ala Val Glu
                85                  90                  95

Arg Tyr Leu Gln Asp Gln Gln Leu Leu Gly Ile Trp Gly Cys Ser Gly
            100                 105                 110

Lys Leu Ile Cys Thr Thr Ser Val Pro Trp Asn Asp Ser Trp Ser Asn
        115                 120                 125

Lys Thr Tyr Gly Glu Ile Trp Gly Asn Met Thr Trp Met Gln Trp Asp
    130                 135                 140

Arg Glu Ile Asn Asn Tyr Thr Gly Leu Ile Tyr Thr Leu Leu Glu Glu
145                 150                 155                 160

Ser Gln His Gln Gln Glu Lys Asn Glu Gln Asp Leu Leu Ala Leu Asp
                165                 170                 175

Gln Trp Ala Ser Leu Trp Asn Trp Phe Asp Ile Ser Asn Trp Leu Trp
            180                 185                 190

Tyr Ile Lys Ile Phe Ile Met Ile Val Gly Gly Leu Ile Gly Leu Arg
        195                 200                 205

Ile Val Phe Ala Val Leu Ser Ile Val Asn Arg Val Arg Gln Gly Tyr
    210                 215                 220

Ser Pro Leu Ser Phe Gln Thr His Phe Pro Ala Pro Arg Gly Pro Asp
225                 230                 235                 240

Arg Pro Glu Gly Thr Glu Glu Glu Gly Gly Glu Arg Asp Arg Asp Arg
                245                 250                 255

Ser Thr Arg Leu Val His Gly Leu Leu Pro Leu Val Trp Asp Asp Leu
            260                 265                 270

Arg Ser Leu Cys Leu Phe Ser Tyr His Arg Leu Arg Asp Leu Leu Leu
        275                 280                 285

Ile Ala Ala Arg Ile Val Glu Leu Leu Gly Arg Arg Gly Trp Glu Ala
    290                 295                 300
```

-continued

```
Leu Lys Tyr Arg Trp Asn Leu Leu Gln Tyr Trp Leu Gln Glu Leu Lys
305                 310                 315                 320

Asn Ser Ala Val Ser Leu Tyr Asn Thr Thr Ala Ile Val Val Ala Glu
                325                 330                 335

Gly Thr Asp Arg Val Ile Glu Val Val Gln Arg Ala Cys Arg Ala Ile
            340                 345                 350

Tyr His Ile Pro Arg Arg Ile Arg
        355                 360
```

<210> SEQ ID NO 62
<211> LENGTH: 359
<212> TYPE: PRT
<213> ORGANISM: Human immunodeficiency virus

<400> SEQUENCE: 62

```
Lys Ile Glu Pro Leu Gly Val Ala Pro Thr Lys Ala Lys Arg Arg Val
  1               5                  10                  15

Val Gln Arg Glu Lys Arg Ala Val Gly Ile Gly Ala Met Phe Leu Gly
             20                  25                  30

Phe Leu Gly Ala Ala Gly Ser Thr Met Gly Ala Ala Ser Leu Thr Leu
         35                  40                  45

Thr Val Gln Ala Arg Gln Leu Leu Ser Gly Ile Val Gln Gln Gln Asn
     50                  55                  60

Asn Leu Leu Arg Ala Ile Glu Ala Gln Gln His Leu Leu Gln Leu Thr
 65                  70                  75                  80

Val Trp Gly Ile Lys Gln Leu Gln Ala Arg Val Leu Ala Val Glu Arg
                 85                  90                  95

Tyr Leu Lys Asp Gln Gln Leu Leu Gly Ile Trp Gly Cys Ser Gly Lys
            100                 105                 110

Leu Ile Cys Thr Thr Ala Val Pro Trp Asn Asp Ser Trp Ser Asn Lys
        115                 120                 125

Thr Met Asp Gln Ile Trp Asn Asn Met Thr Trp Met Asp Trp Glu Lys
    130                 135                 140

Glu Ile Asp Asn Tyr Thr Ser Leu Ile Tyr Asn Leu Ile Glu Glu Ser
145                 150                 155                 160

Gln Asn Gln Gln Asp Lys Asn Glu Gln Glu Leu Leu Glu Leu Asp Lys
                165                 170                 175

Trp Ala Ser Leu Trp Asn Trp Phe Asn Ile Thr Asn Trp Leu Trp Tyr
            180                 185                 190

Ile Lys Ile Phe Ile Met Ile Ile Gly Gly Leu Val Gly Leu Arg Ile
        195                 200                 205

Val Phe Ala Val Val Ser Ile Val Asn Arg Val Arg Gln Gly Tyr Ser
    210                 215                 220

Pro Leu Ser Phe Gln Thr Arg Leu Pro Ala Pro Arg Gly Pro Asp Arg
225                 230                 235                 240

Pro Glu Gly Ile Glu Glu Glu Gly Gly Glu Gln Asp Arg Asp Arg Ser
                245                 250                 255

Gly Arg Leu Val Asp Gly Leu Leu Ala Leu Ile Trp Val Asp Leu Arg
            260                 265                 270

Ser Leu Cys Leu Phe Ser Tyr His Arg Leu Arg Asp Leu Leu Leu Ile
        275                 280                 285

Leu Thr Arg Ile Val Glu Leu Leu Gly Arg Arg Gly Trp Glu Ala Leu
    290                 295                 300

Lys Tyr Trp Trp Asn Leu Leu Gln Tyr Trp Ser Gln Glu Leu Lys Thr
```

-continued

```
305                 310                 315                 320

Ser Ala Val Asn Leu Leu Asn Ala Thr Ala Ile Ala Val Ala Glu Gly
                325                 330                 335

Thr Asp Arg Val Ile Glu Val Val Gln Arg Ala Tyr Arg Ala Leu Leu
            340                 345                 350

His Ile Pro Thr Arg Ile Arg
        355
```